United States Patent
Astier et al.

(10) Patent No.: US 12,121,896 B2
(45) Date of Patent: Oct. 22, 2024

(54) NUCLEIC ACID SEQUENCING BY SYNTHESIS USING MAGNETIC SENSOR ARRAYS

(71) Applicants: Roche Sequencing Solutions, Inc., Pleasanton, CA (US); Western Digital Technologies, Inc., San Jose, CA (US)

(72) Inventors: Yann Astier, Pleasanton, CA (US); Patrick Braganca, San Jose, CA (US); Juraj Topolancik, Redwood City, CA (US)

(73) Assignees: Roche Sequencing Solutions, Inc., Pleasanton, CA (US); Sandisk Technologies, Inc., Milpitas, CA (US)

( * ) Notice: Subject to any disclaimer, the term of this patent is extended or adjusted under 35 U.S.C. 154(b) by 529 days.

(21) Appl. No.: 17/602,319

(22) PCT Filed: Apr. 8, 2020

(86) PCT No.: PCT/US2020/027290
§ 371 (c)(1),
(2) Date: Oct. 8, 2021

(87) PCT Pub. No.: WO2020/210370
PCT Pub. Date: Oct. 15, 2020

(65) Prior Publication Data
US 2022/0193670 A1 Jun. 23, 2022

Related U.S. Application Data
(60) Provisional application No. 62/833,130, filed on Apr. 12, 2019.

(51) Int. Cl.
*B01L 3/00* (2006.01)
*G01N 27/08* (2006.01)
(Continued)

(52) U.S. Cl.
CPC ........ *B01L 3/502715* (2013.01); *G01N 27/08* (2013.01); *G01N 27/74* (2013.01);
(Continued)

(58) Field of Classification Search
CPC ....... B01L 2200/027; B01L 2200/0652; B01L 2300/0645; B01L 2300/0663;
(Continued)

(56) References Cited

U.S. PATENT DOCUMENTS
| | | |
|---|---|---|
| 5,200,084 A | 4/1993 | Liberti et al. |
| 5,302,509 A | 4/1994 | Cheeseman |

(Continued)

FOREIGN PATENT DOCUMENTS
| | | |
|---|---|---|
| CN | 102928596 A | 2/2013 |
| CN | 103885000 A | 6/2014 |

(Continued)

OTHER PUBLICATIONS

Hanqiao Zhang et al., Broadband Mag-Noise of Patterned Permalloy Thin Films,: IEEE Trans. on Magnetics, vol. 46, No. 6, Jun. 2010, pp. 2442-2445.

(Continued)

*Primary Examiner* — Jennifer Wecker

(57) ABSTRACT

Disclosed herein are apparatuses for nucleic acid sequencing, and methods of making and using such apparatuses. In some embodiments, the apparatus comprises a magnetic sensor array comprising a plurality of magnetic sensors, each of the plurality of magnetic sensors coupled to at least one address line, at least one selector element, and a fluid chamber adjacent to the magnetic sensor array, the fluid chamber having a proximal wall adjacent to the magnetic sensor array.

A method of manufacturing sequencing device comprises fabricating a first addressing line on a substrate, fabricating (Continued)

a plurality of magnetic sensors such that the bottom portion of each sensor is coupled to the first addressing line, depositing a dielectric material between the sensors, fabricating additional addressing lines coupled to the top portions of the sensors, and removing a portion of the dielectric material adjacent to the sensors to create a fluid chamber.

23 Claims, 22 Drawing Sheets

(51) Int. Cl.
G01N 27/74 (2006.01)
G01N 33/58 (2006.01)
C12Q 1/6869 (2018.01)

(52) U.S. Cl.
CPC .......... *G01N 33/58* (2013.01); *B01L 2200/12* (2013.01); *B01L 2300/0663* (2013.01); *B01L 2300/0896* (2013.01); *B01L 2300/12* (2013.01); *C12Q 1/6869* (2013.01)

(58) Field of Classification Search
CPC ......... B01L 2300/0864; B01L 2300/12; B01L 2400/0415; B01L 2400/0439; B01L 3/502715; B01L 3/50273; B01L 3/502761; C12Q 3/00; G01N 15/1023; G01N 15/1031; G01N 2015/0019; G01N 2015/1006; G01N 2015/1027; G01N 2015/1028
See application file for complete search history.

(56) References Cited

U.S. PATENT DOCUMENTS

| | | | |
|---|---|---|---|
| 6,037,167 A | 3/2000 | Adelman et al. |
| 6,046,585 A | 4/2000 | Simmonds |
| 6,197,520 B1 | 3/2001 | Wittwer et al. |
| 6,406,848 B1 | 6/2002 | Bridgham et al. |
| 6,654,505 B2 | 11/2003 | Bridgham et al. |
| 6,806,052 B2 | 10/2004 | Bridgham et al. |
| 6,831,994 B2 | 12/2004 | Bridgham et al. |
| 6,833,246 B2 | 12/2004 | Balasubramanian |
| 6,905,736 B1 | 6/2005 | Chow et al. |
| 6,969,488 B2 | 11/2005 | Bridgham et al. |
| 6,969,679 B2 | 11/2005 | Okamura et al. |
| 7,057,026 B2 | 6/2006 | Barnes et al. |
| 7,115,400 B1 | 10/2006 | Adessi et al. |
| 7,282,370 B2 | 10/2007 | Bridgham et al. |
| 7,382,586 B2 | 6/2008 | Carey et al. |
| 7,405,281 B2 | 7/2008 | Xu et al. |
| 7,414,116 B2 | 8/2008 | Milton et al. |
| 7,427,673 B2 | 9/2008 | Balasubramanian et al. |
| 7,473,031 B2 | 1/2009 | Wolkin et al. |
| 7,541,444 B2 | 6/2009 | Milton et al. |
| 7,566,537 B2 | 7/2009 | Balasubramanian et al. |
| 7,771,973 B2 | 8/2010 | Milton et al. |
| 7,772,384 B2 | 8/2010 | Balasubramanian et al. |
| 7,920,032 B2 | 4/2011 | Makinwa et al. |
| 8,053,244 B2 | 11/2011 | Ryan et al. |
| 8,058,031 B2 | 11/2011 | Xu et al. |
| 8,071,739 B2 | 12/2011 | Milton et al. |
| 8,130,072 B2 | 3/2012 | De Bruyker et al. |
| 8,158,346 B2 | 4/2012 | Balasubramanian et al. |
| 8,252,910 B2 | 8/2012 | Korlach et al. |
| 8,259,409 B2 | 9/2012 | Braganca et al. |
| 8,361,713 B2 | 1/2013 | Bridgham et al. |
| 8,367,813 B2 | 2/2013 | Korlach |
| 8,432,644 B2 | 4/2013 | Braganca et al. |
| 8,462,461 B2 | 6/2013 | Braganca et al. |
| 8,513,029 B2 | 8/2013 | Zhou |
| 8,553,346 B2 | 10/2013 | Braganca et al. |
| 8,570,677 B2 | 10/2013 | Braganca et al. |
| 8,597,881 B2 | 12/2013 | Milton et al. |
| 8,652,810 B2 | 2/2014 | Adessi et al. |
| 8,654,465 B2 | 2/2014 | Braganca et al. |
| 8,675,309 B2 | 3/2014 | Braganca et al. |
| 8,728,729 B2 | 5/2014 | Bridgham et al. |
| 8,728,825 B2 | 5/2014 | Wang et al. |
| 9,121,062 B2 | 9/2015 | Balasubramanian et al. |
| 9,273,354 B2 | 3/2016 | Bridgham et al. |
| 9,297,006 B2 | 3/2016 | Adessi et al. |
| 9,435,791 B2 | 9/2016 | Acosta et al. |
| 9,453,258 B2 | 9/2016 | Kain et al. |
| 9,464,107 B2 | 10/2016 | Wegener et al. |
| 9,587,275 B2 | 3/2017 | Emig et al. |
| 9,605,310 B2 | 3/2017 | Balasubramanian et al. |
| 9,640,748 B2 | 5/2017 | Gotsmann et al. |
| 10,203,379 B2 | 2/2019 | Wang et al. |
| 10,260,095 B2 | 4/2019 | Esfandyarpour et al. |
| 10,591,440 B2 | 3/2020 | Astier et al. |
| 11,112,468 B2 | 9/2021 | Braganca |
| 2004/0043479 A1 | 3/2004 | Briscoe et al. |
| 2004/0219695 A1 | 11/2004 | Fox |
| 2005/0054081 A1 | 3/2005 | Hassard et al. |
| 2005/0087000 A1 | 4/2005 | Coehoorn et al. |
| 2005/0100930 A1 | 5/2005 | Wang et al. |
| 2005/0118102 A1 | 6/2005 | Xiang et al. |
| 2007/0224700 A1 | 9/2007 | Masters |
| 2007/0264159 A1 | 11/2007 | Graham et al. |
| 2008/0218165 A1 | 9/2008 | Kahlman et al. |
| 2008/0241569 A1 | 10/2008 | Qin et al. |
| 2009/0148857 A1 | 6/2009 | Srivastava et al. |
| 2009/0206832 A1 | 8/2009 | Kahlman et al. |
| 2009/0208957 A1 | 8/2009 | Korlach et al. |
| 2010/0039105 A1 | 2/2010 | Ryan et al. |
| 2010/0111768 A1 | 5/2010 | Banerjee et al. |
| 2010/0194386 A1 | 8/2010 | Prins et al. |
| 2010/0207631 A1 | 8/2010 | McDowell |
| 2010/0231214 A1 | 9/2010 | Zhou |
| 2010/0248973 A1 | 9/2010 | Lankvelt et al. |
| 2010/0291558 A1 | 11/2010 | Kim |
| 2011/0223612 A1 | 9/2011 | Wang et al. |
| 2012/0214171 A1 | 8/2012 | Kotseroglou |
| 2012/0295262 A1 | 11/2012 | Ronaghi et al. |
| 2014/0008281 A1 | 1/2014 | Ramanathan et al. |
| 2014/0099663 A1 | 4/2014 | Wang et al. |
| 2014/0139214 A1 | 5/2014 | Park et al. |
| 2014/0292318 A1 | 10/2014 | Wang et al. |
| 2016/0131613 A1 | 5/2016 | Jayant et al. |
| 2016/0139035 A1* | 5/2016 | Florescu ................. B01L 3/561 506/40 |
| 2017/0097337 A1 | 4/2017 | Shultz et al. |
| 2017/0304825 A1 | 10/2017 | Issadore et al. |
| 2018/0074016 A1 | 3/2018 | Chen et al. |
| 2018/0100190 A1 | 4/2018 | Esfandyarpour et al. |
| 2018/0128822 A1 | 5/2018 | Wang et al. |
| 2018/0237850 A1 | 8/2018 | Mandell et al. |
| 2018/0284200 A1 | 10/2018 | Chen et al. |
| 2019/0032114 A1 | 1/2019 | Trivedi |
| 2019/0170680 A1 | 6/2019 | Sikora et al. |
| 2019/0390267 A1 | 12/2019 | Astier et al. |
| 2020/0324283 A1 | 10/2020 | Braganca et al. |
| 2020/0326309 A1 | 10/2020 | Braganca et al. |
| 2020/0326335 A1 | 10/2020 | Braganca et al. |
| 2020/0326392 A1 | 10/2020 | Braganca et al. |
| 2021/0047681 A1 | 2/2021 | Mendonsa et al. |
| 2021/0047682 A1 | 2/2021 | Mendonsa et al. |
| 2021/0079455 A1 | 3/2021 | Braganca et al. |

FOREIGN PATENT DOCUMENTS

| | | |
|---|---|---|
| CN | 105112516 A | 12/2015 |
| CN | 107873060 A | 4/2018 |
| CN | 107923910 A | 4/2018 |
| CN | 108138229 A | 6/2018 |
| CN | 107051597 B | 8/2019 |
| EP | 1544310 A2 | 6/2005 |
| EP | 2674264 A2 | 12/2013 |
| EP | 3208627 A1 | 8/2017 |
| ES | 2674264 | 6/2018 |
| WO | 2005047864 A3 | 9/2005 |

(56) References Cited

FOREIGN PATENT DOCUMENTS

| WO | 2005124345 | A2 | | 12/2005 | | |
| --- | --- | --- | --- | --- | --- | --- |
| WO | WO-2009001280 | A2 | * | 12/2008 | ........... | H01L 21/568 |
| WO | 2015031691 | A1 | | 3/2015 | | |
| WO | 2016183218 | A1 | | 11/2016 | | |
| WO | 2017030999 | A1 | | 2/2017 | | |
| WO | 2017061129 | A1 | | 4/2017 | | |
| WO | 2018017884 | A1 | | 1/2018 | | |
| WO | 2018186539 | A1 | | 10/2018 | | |
| WO | 2018226876 | A1 | | 12/2018 | | |
| WO | 2019060628 | A1 | | 3/2019 | | |
| WO | 2019068204 | A1 | | 4/2019 | | |

OTHER PUBLICATIONS

Daschiel et al. The holy grail of microfluidics: sub-laminar drag by layout of periodically embedded microgrooves (2013) MicrofluidNanofluid 15, 675-687.

International Search Report and Written Opinion from PCT Application No. PCT/US2021/040767 (filed Jul. 8, 2021), mailed Oct. 25, 2021.

Mao et al. A Microfluidic Device with a Linear Temperature Gradient for Parallel and Combinatorial Measurements (2002) J AmChem Soc 124, 4432-4435.

Qiu et al. Instrument-free point-of-care molecular diagnosis of H 1 N 1 based on microfluidic convective PCR (2017) Sensors andActuators B: Chemical 243, 738-744.

A. Seki, et al., "Study of the heating characteristics and mechanisms of magnetic nanoparticles over a wide range of frequencies and amplitudes of an alternating magnetic field," Journal of Physics: Conference Series 521 (2014).

A.M. Sydor et al., "Super-Resolution Microscopy: From Single Molecules to Supramolecular Assemblies," Trends in Cell Biology, Dec. 2015, vol. 25, No. 12, pp. 730-748.

B. N. Engel, et al., "A 4-Mb Toggle MRAM Based on a Novel Bit and Switching Method," IEEE Transactions on Magnetics, vol. 41, No. 1, Jan. 2005.

C. Chappert et al., "The emergence of spin electronics in data storage," Nature Materials, Dec. 2007.

C.H. Smith et al., "High-resolution giant magnetoresistance on-chip arrays for magnetic imaging," Journal of Applied Physics 93, 6864 (2003).

D. Ross et al., "Temperature Measurement in Microfluidic Systems Using a Temperature-Dependent Fluorescent Dye," Anal. Chem. 2001, 73, 17, 4117-4123, Jul. 24, 2001.

E. du Trémolet de Lacheisserie, D. Gignoux, and M. Schlenker (editors), Magnetism: Materials and Applications, vol. 2. Springer, 2005.

E. Hall, "On a New Action of the Magnet on Electric Currents," American Journal of Mathematics, vol. 2, 287, 1879.

ePHOTOzine.com, "Complete Guide To Image Sensor Pixel Size," Aug. 2, 2016, available at https://www.ephotozine.com/article/complete-guide-to-image-sensor-pixel-size-29652.

F. Grasset et al., "Synthesis, magnetic properties, surface modification and cytotoxicity evaluation of Y3Fe5—xAlxO12 (0?x?2) garnet submicron particles for biomedical applications," Journal of Magnetism and Magnetic Materials, vol. 234, Issue 3, Sep. 2001, pp. 409-418.

F. Menges et al., "Temperature mapping of operating nanoscale devices by scanning probe thermometry," Nature Communications, 7:10874, Mar. 3, 2016.

G. Li, S. Sun, R. J. Wilson, R. L. White, N. Pourmand, S. X. Wang, "Spin valve sensors for ultrasensitive detection of superparamagnetic nanoparticles for biological applications," Sensors and Actuators, vol. 126, 98, 2006.

Illumina, "Illumina CMOS Chip and One-Channel SBS Chemistry," document No. 770-2013-054-B, 2018 (available at https://www.illumina.com/content/dam/illumina-marketing/documents/products/techspotlights/cmos-tech-note-770-2013-054.pdf).

Illumina, "NovaSeq 6000 Sequencing System," 2019, available at https://www.illumina.com/systems/sequencing-platforms/novaseq.html.

International Search Report and Written Opinion from PCT Application No. PCT/US2019/068131 (filed Dec. 20, 2019), mailed Apr. 1, 2020.

International Search Report and Written Opinion from PCT Application No. PCT/US2019/068535 (filed Dec. 26, 2019), mailed Apr. 26, 2020.

International Search Report and Written Opinion from PCT Application No. PCT/US2020/014707 (filed Jan. 23, 2020), mailed May 11, 2020.

International Search Report and Written Opinion from PCT Application No. PCT/US2020/021776 (filed Mar. 9, 2020), mailed Sep. 1, 2020.

International Search Report and Written Opinion from PCT Application No. PCT/US2020/023069 (filed Mar. 17, 2020), mailed Jul. 20, 2020.

International Search Report and Written Opinion from PCT Application No. PCT/US2020/023078 (filed Mar. 17, 2020), mailed Jul. 19, 2020.

International Search Report and Written Opinion from PCT Application No. PCT/US2020/027290 (filed Apr. 8, 2020), mailed Jun. 25, 2020.

International Search Report and Written Opinion from PCT Application No. PCT/US2020/035915 (filed Jun. 3, 2020), mailed Aug. 26, 2020.

International Search Report and Written Opinion from PCT Application No. PCT/US2021/021274 (filed Mar. 7, 2021), mailed Sep. 28, 2021.

International Search Report and Written Opinion from PCT Application No. PCT/US2021/028263 (filed Apr. 21, 2021), mailed Aug. 26, 2021.

International Search Report from PCT App. No. PCT/US2016/046888, mailed Oct. 26, 2016.

J. C. Slonczewski, "Current-driven excitation of magnetic multilayers," Journal of Magnetism and Magnetic Materials, vol. 159, L1, 1996.

J. Sakakibara et al., "Measurements of thermally stratified pipe flow using image-processing techniques," Experiments in Fluids, Dec. 1993, vol. 16, Issue 2, pp. 82-96.

John Pearce, et al., "Magnetic Heating of Nanoparticles: The Importance of Particle Clustering to Achieve Therapeutic Temperatures," Journal of Nanotechnology in Engineering and Medicine, Feb. 2014, vol. 4 / 011007-1.

L. Berger, "Emission of spin waves by a magnetic multilayer traversed by a current," Physical Review B, vol. 54, 9353, 1996.

Lany, M., G. Boero, and R. S. Popovic. "Superparamagnetic microbead inductive detector". Review of scientific instruments 76.8 (2005): 084301.

Latha, G., Kumar, P. D., Gopi, K., Srikanth, P., Kusumalatha, Y., & Babu, G. V. (2017). A review on magnetic micro/nanoparticles. World J. Pharm. Res, 6, 341-366.

Lin Gui and Carolyn L. Ren, "Temperature measurement in microfluidic chips using photobleaching of a fluorescent thin film," Applied Physics Letters 92, 024102, 2008.

M. Aslam et al., "Silica encapsulation and magnetic properties of FePt nanoparticles," Journal of Colloid and Interface Science 290 (2005) 444-449.

M. Díaz-Michelena, "Small Magnetic Sensors for Space Applications," Sensors, vol. 9, 2271, 2009.

M. Hisham Alnasir et al., "Magnetic and magnetothermal studies of pure and doped gadolinium silicide nanoparticles for self-controlled hyperthermia applications," Journal of Magnetism and Magnetic Materials, vol. 449, Mar. 1, 2018, pp. 137-144.

M.T. Tlili et al., "Magnetic, Electrical Properties and Spin-Glass Effect of Substitution of Ca for Pr in Ca2—xPrxMnO4 Compounds," The Open Surface Science Journal, 2009, vol. 1, pp. 54-58.

Michael L. Metzker, "Sequencing Technologies—the Next Generation," Nature Rev. Genet. 11: 31-46 (2009).

Miller, M. M., et al. "A DNA array sensor utilizing magnetic microbeads and magnetoelectronic detection". Journal of Magnetism and Magnetic Materials 225.1-2 (2001): 138-144.

(56) References Cited

OTHER PUBLICATIONS

N. X. Phuc, et al., "Tuning of the Curie Temperature in La1—xSrxMn1—yTiyO3" J. Korean Phy. Soc., vol. 52, No. 5, May 2008, pp. 1492-1495.

N.R. Patil et al., "Effect of temperature on the fluorescence emission of ENCTTTC in different nonpolar solvents," Can. J. Phys. 91: 971-975 (2013).

P. Anderson, J. Rowell, "Probable Observation of the Josephson Superconducting Tunneling Effect," Physical Review Letters, vol. 10, 230, 1963.

P. M. Braganca, B. A. Gurney, B. A. Wilson, J. A. Katine, S. Maat and J. R. Childress, "Nanoscale magnetic field detection using a spin torque oscillator," Nanotechnology, vol. 21, 235202, 2010.

P. Namdari, H. Daraee, and A. Eatemadi, "Recent Advances in Silicon Nanowire Biosensors: Synthesis Methods, Properties and Applications", Nanoscale Research Letters, vol. 11, 406, 2016.

Quynh, L. K., et al. Detection of magnetic nanoparticles using simple AMR sensors in Wheatstone bridge. Journal of Science: Advanced Materials and Devices, 2016, 1.1: 98-102.

R. C. Jaklevic, J. Lambe, A. H. Silver & J. E. Mercereau, "Quantum Interference Effects in Josephson Tunneling," Physical Review Letters, vol. 12, 159, 1964.

R. Giri, "Temperature effect study upon the fluorescence emission of substituted coumarins," Spectrochimica Acta Part A: Molecular Spectroscopy, vol. 48, Issue 6, Jun. 1992, p. 843-848.

R. Sato, K. Kudo, T. Nagasawa, H. Suto, and K. Mizushima, "Simulations and Experiments Toward High-Data-Transfer-Rate Readers Composed of a Spin-Torque Oscillator," IEEE Transactions On Magnetics, vol. 48, 1758, 2012.

Rabehi, A., Electromagnetic microsystem for the detection of magnetic nanoparticles in a microfluidic structure for immunoassays (Doctoral dissertation). Jan. 29, 2020.

Rauwerdink, A. M., Giustini, A. J., & Weaver, J. B. (2010). Simultaneous quantification of multiple magnetic nanoparticles. Nanotechnology, 21(45), 455101.

Riedinger, A., Guardia, P., Curcio, A., Garcia, M. A., Cingolani, R., Manna, L., & Pellegrino, T. (2013). Subnanometer local temperature probing and remotely controlled drug release based on azo-functionalized iron oxide nanoparticles. Nano letters, 13(6), 2399-2406.

European Patent Office, Communication pursuant to Article 94(3) EPC in EP application No. 20722872.7, mailed Aug. 2, 2023.

First Office Action Issued by China National Intellectual Property Administration in CN App. No. 202080034586.7, mailed Aug. 16, 2022.

Second Office Action Issued by China National Intellectual Property Administration in CN App. No. 202080034586.7, mailed Feb. 24, 2023.

S. Dutz and R. Hergt, "Magnetic nanoparticle heating and heat transfer on a microscale: Basic principles, realities and physical limitations of hyperthermia for tumour therapy," Int J Hyperthermia, 2013; 29(8): 790-800.

S.I. Kiselev et al., "Microwave oscillations of a nanomagnet driven by a spin-polarized current," Nature 425, pp. 380-383, 2003.

Srimani T. et al., "High Sensitivity Biosensor using Injection Locked Spin Torque Nano-Oscillators," arXiv:1511.09072, Nov. 2015.

T. Nagasawa et al., "Delay detection of frequency modulation signal from a spin-torque oscillator under a nanosecond-pulsed magnetic field," Journal of Applied Physics, vol. 111, 07C908 (2012).

Tang, C., He, Z., Liu, H., Xu, Y., Huang, H., Yang, G., . . . & Chen, Z. (2020). Application of magnetic nanoparticles in nucleic acid detection. Journal of Nanobiotechnology, 18, 1-19. Apr. 21, 2020.

W. Andrä et al., "Temperature distribution as function of time around a small spherical heat source of local magnetic hyperthermia," Journal of Magnetism and Magnetic Materials, vol. 194, Issues 1-3, Apr. 1999, pp. 197-203.

Wang, W., & Jiang, Z., "Thermally assisted magnetic tunneling junction for biosensing applications," IEEE Transactions on Magnetics, 43(6), 2406-2408, Jun. 30, 2007.

Weifeng Shen et al., "Detection of DNA labeled with magnetic nanoparticles using MgO-based magnetic tunnel junction sensors," Journal of Applied Physics 103, 07A306 (2008).

Weijun Zhou, et al., "Novel dual fluorescence temperature-sensitive chameleon DNA-templated nanocluster pair for intracellular thermometry" Nano Research (2018), vol. 11, pp. 2012-2023, Mar. 19, 2018, https://doi.org/10.1007/s12274-017-1817-7 Mar. 19, 2018 (Mar. 19, 2018).

Xia, Haiyan et al., "Micromagnetic simulation for detection of magnetic nanobeads by spin torque oscillator," Journal of Magnetism and Magnetic Materials 2017, vol. 432, pp. 387-390, Feb. 4, 2017.

Y.-C. Liang, L. Chang, W. Qiu, A. G. Kolhatkar, B. Vu, K. Kourentzi, T. R. Lee, Y. Zu, R. Willson, and D. Litvinov, "Ultrasensitive Magnetic Nanoparticle Detector for Biosensor Applications," Sensors, vol. 17, 1296, 2017.

Ye, F., Zhao, Y., El-Sayed, R., Muhammed, M., & Hassan, M. (2018). Advances in nanotechnology for cancer biomarkers. Nano Today, 18, 103-123.

Yu, L., Liu, J., Wu, K., Klein, T., Jiang, Y., & Wang, J. P. (2014). Evaluation of hyperthermia of magnetic nanoparticles by dehydrating DNA. Scientific reports, 4, 7216.

Mohamad, O. and Ho, W. S., "The Next Generation Sequencing Technologies," Jilid 18 No. 1 &2/ISSN 1394-5750 Jan. & Jul. 2011.

S. Brinkers et al., "The persistence length of double stranded DNA determined using dark field tethered particle motion," The Journal of Chemical Physics 130, 215105, Jun. 2009.

\* cited by examiner

Immobilized Polymerase

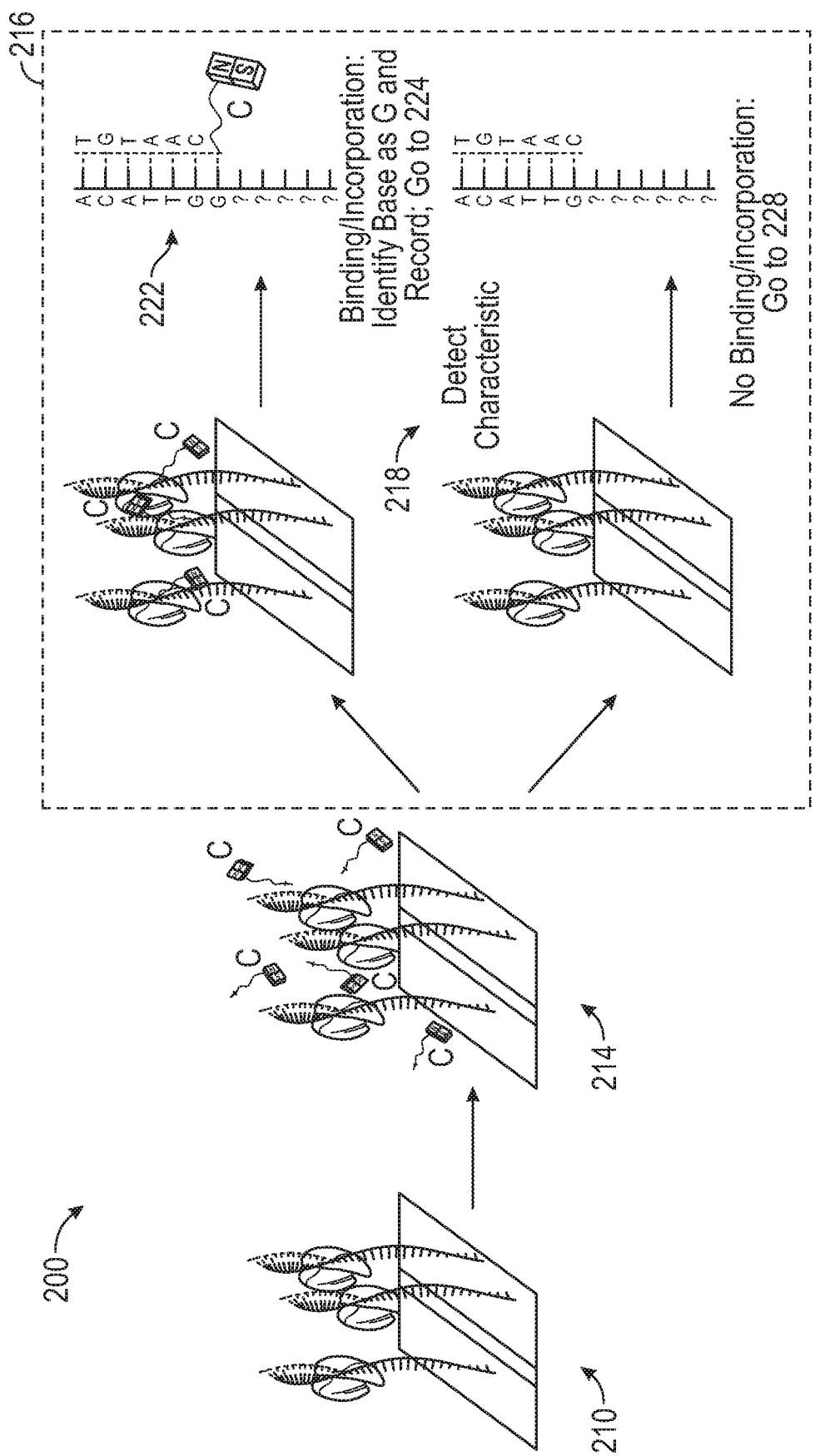

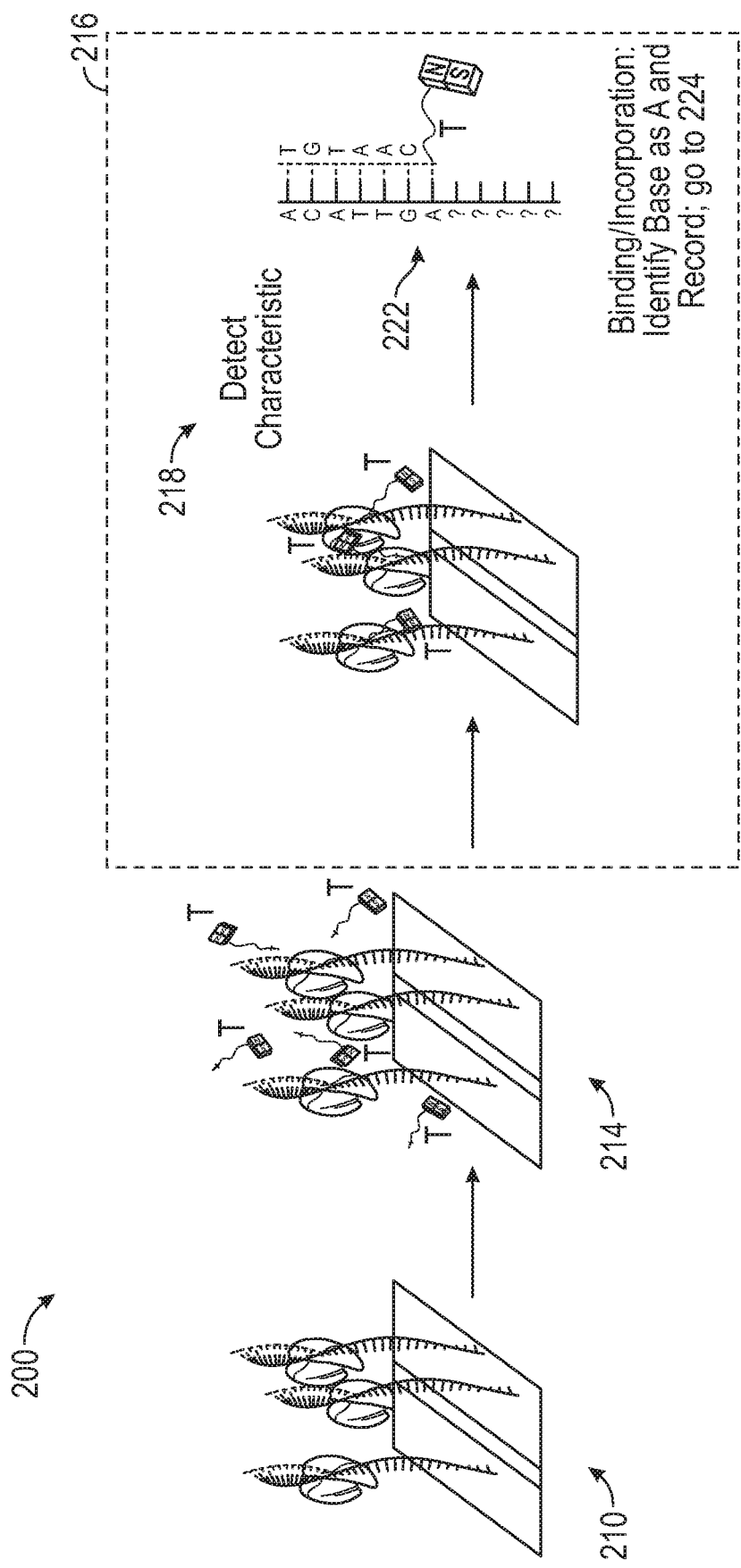

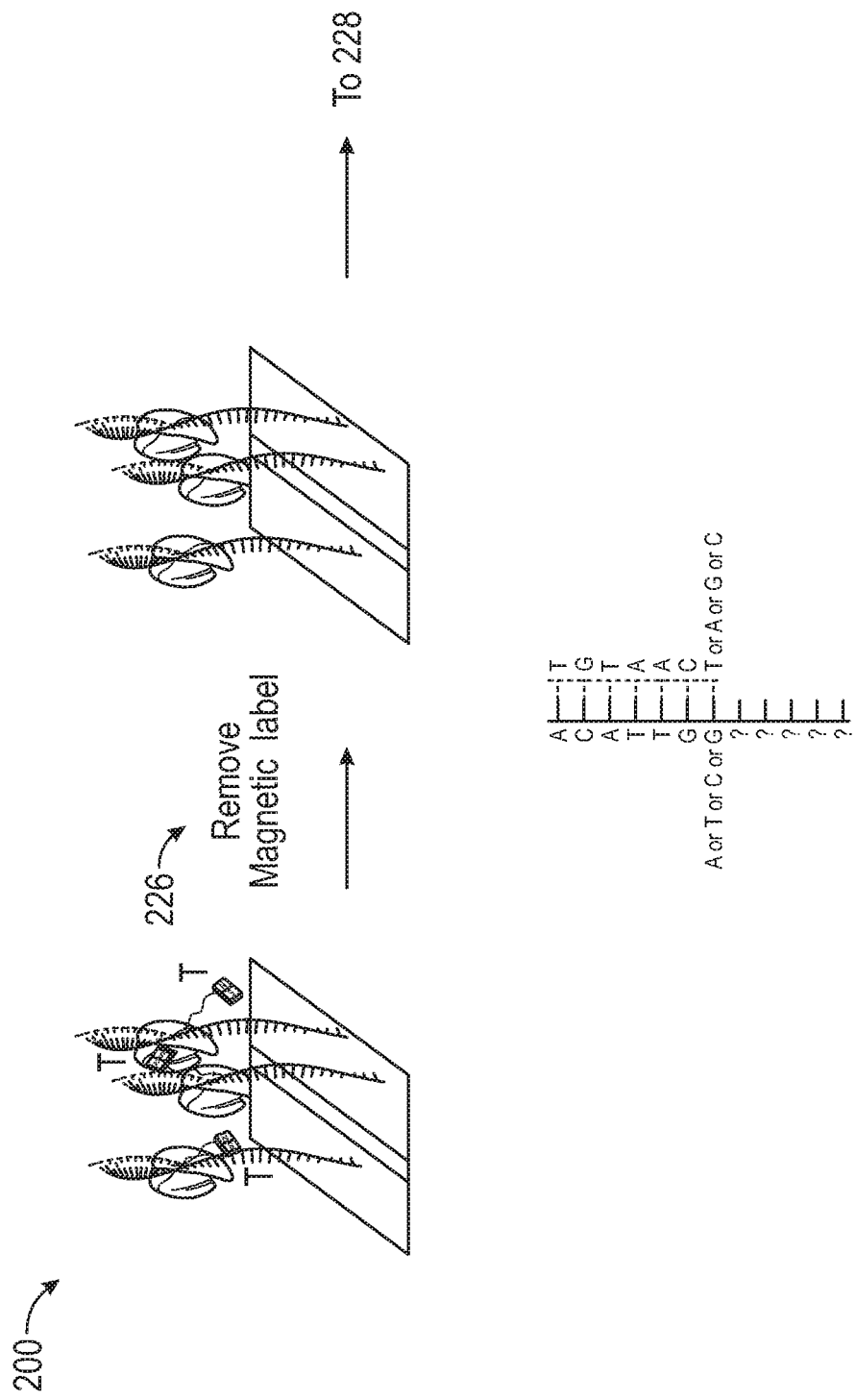

NUCLEIC ACID SEQUENCING BY SYNTHESIS USING MAGNETIC SENSOR ARRAYS

CROSS-REFERENCE TO RELATED APPLICATIONS

Sequencing by synthesis (SBS) has been a successful commercially-viable method to obtain large quantities of DNA sequencing data. SBS involves binding of primer-hybridized template DNA, incorporation of a deoxynucleoside triphosphate (dNTP), and detection of incorporated dNTP.

BACKGROUND

Sequencing by synthesis (SBS) has been a successful commercially-viable method to obtain large quantities of DNA sequencing data. SBS involves binding of primer-hybridized template DNA, incorporation of a deoxynucleoside triphosphate (dNTP), and detectiTHIon of incorporated dNTP.

Current sequencing systems use fluorescence signal detection. Four fluorescently-labeled nucleotides are used to sequence millions of clusters in parallel. DNA polymerase catalyzes the incorporation of fluorescently-labeled dNTPs into a DNA template strand during sequential cycles of DNA synthesis. During each cycle, a single labeled dNTP is added to the nucleic acid chain. The nucleotide label serves as a "reversible terminator" for polymerization. After the dNTP has been incorporated, the fluorescent dye is identified through laser excitation and imaging, then enzymatically cleaved to allow the next round of incorporation. The base is identified directly from signal intensity measurements during each cycle.

State-of-the-art sequencing systems that rely on fluorescence signal detection can provide throughputs of up to 20 billion reads per run. Achieving such performance, however, requires large-area flow cells, high-precision free-space imaging optics, and expensive high-power lasers to generate sufficient fluorescence signals to enable successful base detection.

Two general strategies have enabled a gradual increase in SBS throughput (e.g., characterized by base reads per run). The first approach has been outward scaling, by increasing the size and the number of flow-cells in the sequencers. This approach increases both the cost of reagents and the price of the sequencing system, because it requires additional high-power lasers and high-precision nano-positioners.

The second approach involves inward scaling, where the size of individual DNA testing sites is reduced so that the number of sequenced DNA strands in a fixed-size flow-cell is higher. This second approach is more appealing to reduce the overall sequencing cost because additional cost only involves implementation of better imaging optics while keeping the cost of consumables the same. But higher numerical aperture (NA) lenses must be employed to distinguish the signal from neighboring fluorophores. This approach has limits because the Rayleigh criterion puts the distance between resolvable light point sources at 0.61 $\lambda$/NA, i.e., even in advanced optical imaging systems, the minimum distance between two sequenced DNA strands cannot be reduced beyond approximately 400 nm. Similar resolution limits apply to sequencing directly on top of imaging arrays where the smallest pixel size achieved so far is less than 1 µm. The Rayleigh criterion currently represents the fundamental limitation for inward scaling of optical SBS systems. Overcoming these limitations may require super-resolution imaging techniques, which has not yet been achieved in highly multiplexed systems. Hence, at this stage, the only practicable way to increase the throughput of optical SBS sequencers is to build bigger flow-cells and more expensive optical scanning and imaging systems.

Thus, there is a need to improve SBS.

SUMMARY

This summary represents non-limiting embodiments of the disclosure.

Disclosed herein are apparatuses for nucleic acid sequencing using magnetic labels (e.g., magnetic particles) and magnetic sensors. Also disclosed are methods of making and using such apparatuses. For simplicity, some of the discussions below refer to sequencing DNA as an example. It is to be understood that the disclosures herein apply generally to nucleic acid sequencing.

The inventors recognized that the resolution limits of fluorescence microscopy and CMOS imagers, as used in prior art SBS, do not apply to electric charge (e.g., silicon nanowire field-effect transistors (FETs)) or magnetic field sensors (e.g., spin valves, magnetic tunnel junctions (MTJs), spin-torque oscillators (STOs), etc.), where the size of sensing elements is an order of magnitude smaller and the level of multiplexing considerably higher than in state-of-the-art SBS systems. Magnetic field sensing in SBS is particularly appealing because DNA and sequencing reagents are non-magnetic, which enables significant improvements to signal-to-noise ratio (SNR) compared to electric charge sensing schemes based on electron transport modulation in CMOS components. Furthermore, magnetic sensing does not require the incorporated bases to be in direct contact with the junction. Miniaturized magnetic field sensors can be used to detect nanoscale magnetic nanoparticles to perform SBS.

Performing SBS using magnetic sensor arrays can dramatically increase the throughput and reduce the cost of sequencing by providing additional inward scaling by a factor of, for example, approximately 100 while eliminating the need for high-power lasers and high-resolution optics in sequencing systems.

This document discloses SBS protocols that use magnetically-labeled nucleotide precursors in conjunction with sequencing devices that include arrays of magnetic sensing elements (e.g., MTJs, STOs, spin valves, etc.). The devices also include one or more etched nanochannels that enable the magnetic sensors to detect the magnetic labels in the magnetically-labeled nucleotide precursors while protecting the magnetic sensors from damage (e.g., using a thin layer of insulator).

In some embodiments, an apparatus for nucleic acid sequencing comprises a magnetic sensor array comprising a plurality of magnetic sensors, each of the plurality of magnetic sensors coupled to at least one address line; and a fluid chamber adjacent to the magnetic sensor array, the fluid chamber having a proximal wall adjacent to the magnetic sensor array. In some embodiments, the magnetic sensor array comprises a linear array. In some embodiments, the proximal wall includes a structure (e.g., a cavity or a ridge) configured to anchor nucleic acid or a nucleic acid polymerase to the proximal wall.

In some embodiments, the apparatus further comprises sensing circuitry coupled to the magnetic sensor array via the at least one address line, wherein the sensing circuitry is configured to apply a current to the at least one address line to detect a characteristic of at least one of the plurality of magnetic sensors, wherein the characteristic indicates a presence or an absence of a magnetically-labeled nucleotide precursor in the fluid chamber. In some embodiments, the characteristic is a magnetic field or a resistance, a change in magnetic field or a change in resistance, or a noise level. In some embodiments, the magnetic sensor comprises a magnetic oscillator, and the characteristic is a frequency of a signal associated with or generated by the magnetic oscillator.

In some embodiments, a surface of the proximal wall comprises polypropylene, gold, glass, or silicon.

In some embodiments, the plurality of magnetic sensors of the array are arranged in a rectangular grid pattern, and the at least one address line includes at least a first address line and a second address line, wherein the first address line identifies a column of the array and the second address line identifies a row of the array.

In some embodiments, a first method of sequencing nucleic acid using the above-described apparatus comprises (a) coupling a plurality of molecules of a nucleic acid polymerase to the proximal wall of the fluid chamber; (b) in one or more rounds of addition, adding, to the fluid chamber, (i) a nucleic acid template comprising a primer binding site and an extendable primer, and (ii) a first magnetically-labeled nucleotide precursor comprising a first cleavable magnetic label, a second magnetically-labeled nucleotide precursor comprising a second cleavable magnetic label, a third magnetically-labeled nucleotide comprising a third cleavable magnetic label, and a fourth magnetically-labeled nucleotide comprising a fourth cleavable magnetic label; and (c) sequencing the nucleic acid template, wherein sequencing the nucleic acid template comprises, using the at least one address line, detecting a characteristic of at least a portion of the magnetic sensors in the magnetic sensor array, wherein the characteristic indicates which of the first, second, third, or fourth magnetically-labeled nucleotide precursors has been incorporated into the extendable primer.

In some embodiments, sequencing the nucleic acid template further comprises, in response to the detecting, recording a complementary base of the incorporated magnetically-labeled nucleotide precursor in a record of a nucleic acid sequence of the nucleic acid template.

In some embodiments, each of the first, second, third, and fourth magnetically-labeled nucleotide precursors is selected from adenine, guanine, cytosine, thymine, or their equivalents.

In some embodiments, two or more of the first, second, third, and fourth cleavable magnetic labels have a same specified magnetic property, and the characteristic used to distinguish the magnetically-labeled nucleotide precursors is one or more of a rate of incorporation, a time taken to incorporate, a frequency-domain characteristic, a time-domain characteristic, a signature of an incorporation process, or a profile of the incorporation process. In some embodiments, each of the first, second, third, and fourth cleavable magnetic labels has a same specified magnetic property, and the characteristic used to distinguish the magnetically-labeled nucleotide precursors is one or more of a rate of incorporation, a time taken to incorporate, a frequency-domain characteristic, a time-domain characteristic, a signature of an incorporation process, or a profile of the incorporation process.

In some embodiments, each of the first, second, third, and fourth cleavable magnetic labels is of a different type, wherein each type has a different magnetic property.

In some embodiments, coupling the plurality of molecules of the nucleic acid polymerase to the proximal wall of the fluid chamber comprises attaching each of the plurality of molecules of the nucleic acid polymerase to a respective bead of a plurality of beads, and attaching the plurality of beads to the proximal wall of the apparatus.

In some embodiments, a second method of sequencing nucleic acid using the above-described apparatus comprises (a) binding a nucleic acid strand to the proximal wall of the apparatus; (b) in one or more rounds of addition, adding, to the fluid chamber, (i) an extendable primer, and (ii) a plurality of molecules of a nucleic acid polymerase; (c) adding, to the fluid chamber, a first magnetically-labeled nucleotide precursor comprising a first cleavable magnetic label; and (d) sequencing the nucleic acid template, wherein sequencing the nucleic acid template comprises, using the at least one address line, detecting a characteristic of at least a first portion of the magnetic sensors in the magnetic sensor array, wherein the characteristic indicates that the first magnetically-labeled nucleotide precursor has bound to at least one molecule of the plurality of molecules of the nucleic acid polymerase or has been incorporated into the extendable primer.

In some embodiments, sequencing the nucleic acid template further comprises, in response to the detecting, recording a complementary base of the first magnetically-labeled nucleotide precursor in a record of a nucleic acid sequence of the nucleic acid strand.

In some embodiments, the second method further comprises amplifying the nucleic acid strand before performing steps (b), (c), and (d).

In some embodiments, the first magnetically-labeled nucleotide precursor is nonextendable by the nucleic acid polymerase, and the second method further comprises, after detecting the characteristic, removing the first cleavable magnetic label and rendering the first magnetically-labeled nucleotide precursor extendable by the nucleic acid polymerase.

In some embodiments, a moiety of the first magnetically-labeled nucleotide precursor is not extendable by the nucleic acid polymerase. In some such embodiments, the moiety of the first magnetically-labeled nucleotide precursor is rendered extendable by chemical cleavage.

In some embodiments, the second method further comprises, after step (c), removing the first cleavable magnetic label by enzymatic or chemical cleavage.

In some embodiments, the second method further comprises repeating steps (c) and (d) with a different magnetically-labeled nucleotide precursor during each repetition. In some such embodiments, each of the first and different magnetically-labeled nucleotide precursors is selected from adenine, guanine, cytosine, thymine, or their equivalents.

In some embodiments, the second method further comprises washing the fluid chamber before step (c).

In some embodiments, the second method further comprises, before detecting the characteristic of the at least a first portion of the magnetic sensors in the magnetic sensor array, adding, to the fluid chamber, a second magnetically-labeled nucleotide precursor comprising a second cleavable magnetic label, and, using the at least one address line, failing to detect the characteristic of the at least a first portion of the magnetic sensors in the magnetic sensor array, wherein the characteristic indicates that the second magnetically-labeled nucleotide precursor has bound to at least one molecule of the plurality of molecules of the nucleic acid polymerase or has been incorporated into the extendable primer.

In some embodiments, the second method further comprises washing the fluid chamber after adding the second magnetically-labeled nucleotide precursor to the fluid chamber.

In some embodiments, the first cleavable magnetic label has a first magnetic property, and the second method further comprises, in the one or more rounds of addition, adding, to the fluid chamber, a second magnetically-labeled nucleotide precursor comprising a second cleavable magnetic label having a second magnetic property, and the characteristic identifies the first magnetic property.

In some embodiments, the second method further comprises, in the one or more rounds of addition, adding, to the fluid chamber, a third magnetically-labeled nucleotide precursor comprising a third cleavable magnetic label having a third magnetic property, and a fourth magnetically-labeled nucleotide precursor comprising a fourth cleavable magnetic label having a fourth magnetic property.

In some embodiments, binding the nucleic acid strand to the proximal wall comprises attaching an adapter to an end of the nucleic acid strand, and coupling an oligonucleotide to the proximal wall of the fluid chamber, wherein the oligonucleotide is complementary to the adapter. In some embodiments, binding the nucleic acid strand to the proximal wall comprises attaching the nucleic acid strand to the proximal wall using a polystyrene or a polyacrylamide gel. In some embodiments, binding the nucleic acid strand to the proximal wall comprises immobilizing the nucleic acid strand via irreversible passive adsorption or affinity between molecules.

In some embodiments, the proximal wall of the apparatus comprises a cavity or a ridge, and binding the nucleic acid strand to the proximal wall comprises applying a hydrogel to the cavity or to the ridge.

In some embodiments, the second method further comprises, after step (b), adding, to the fluid chamber, additional molecules of the nucleic acid polymerase.

In some embodiments of the first or second method, the first cleavable magnetic label comprises a magnetic nanoparticle (e.g., a molecule, a superparamagnetic, or a ferromagnetic nanoparticle).

In some embodiments of the first or second method, the first magnetically-labeled nucleotide precursor comprises one of dATP, dGTP, dCTP, dTTP, or equivalents.

In some embodiments of the first or second method, the nucleic acid polymerase is a Type B polymerase lacking 3'-5' exonuclease activity.

In some embodiments of the first or second method, the nucleic acid polymerase is a thermostable polymerase.

In some embodiments of the first or second method, using the at least one address line comprises applying a current to the at least one address line.

In some embodiments of the first or second method, the characteristic is a magnetic field or a resistance, a frequency of a signal associated with or generated by a magnetic oscillator, a noise level, or a change in magnetic field or a change in resistance. In some embodiments of the first or second method, the characteristic results from a change in magnetic field or a change in resistance.

In some embodiments, a method of manufacturing a nucleic acid sequencing device having at least one fluid chamber configured to contain fluid comprises fabricating a first addressing line, fabricating a plurality of magnetic sensors, each magnetic sensor having a bottom portion and a top portion, wherein each bottom portion is coupled to the first addressing line, depositing a dielectric material between the magnetic sensors, fabricating a plurality of additional addressing lines, each of the plurality of additional addressing lines coupled to the top portion of a respective magnetic sensor of the plurality of magnetic sensors, and removing a portion of the dielectric material adjacent to the plurality of magnetic sensors to create the at least one fluid chamber.

In some embodiments, fabricating comprises depositing. In some embodiments, removing comprises milling or etching.

BRIEF DESCRIPTION OF THE DRAWINGS

Objects, features, and advantages of the disclosure will be readily apparent from the following description of certain embodiments taken in conjunction with the accompanying drawings in which:

FIGS. 11A, 11B, 11C, 11D, 11E, and 11F graphically illustrate the method shown in FIG. 10.

DETAILED DESCRIPTION

Figure 1A:
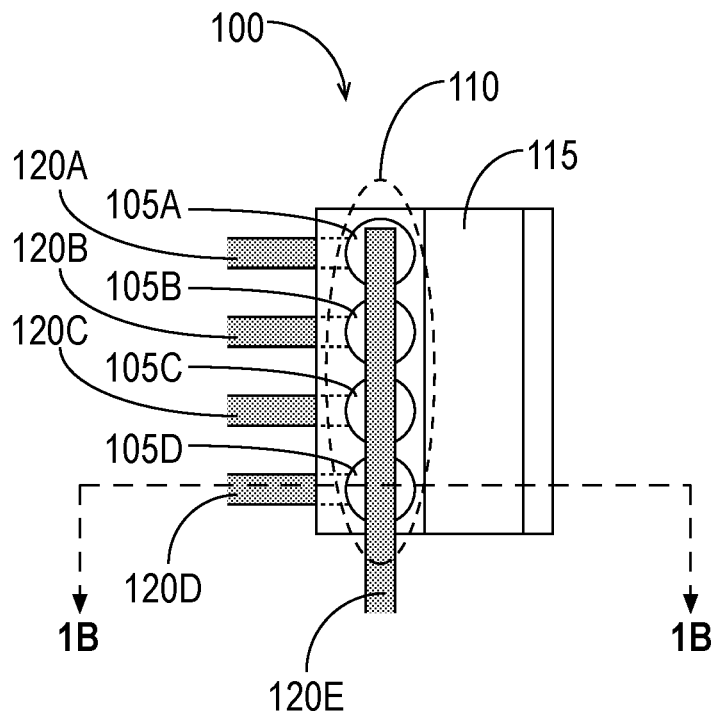
FIGS. 1A, 1B, and 1C illustrate an apparatus for nucleic acid sequencing in accordance with some embodiments.
Figure 1B:
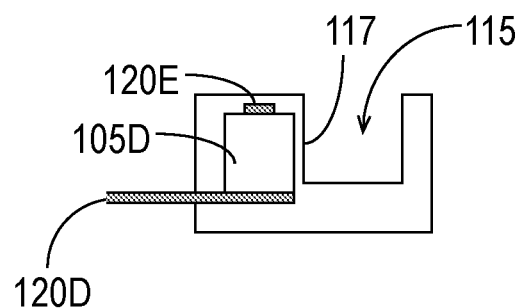
Figure 1C:
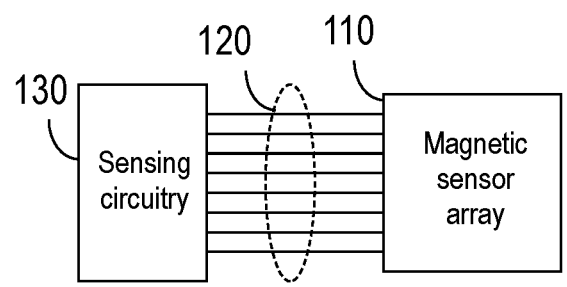

FIGS. 1A, 1B, and 1C illustrate an apparatus 100 for nucleic acid sequencing in accordance with some embodiments. FIG. 1A is a top view of the apparatus, and FIG. 1B is a cross-section view at the position indicated in FIG. 1A. FIG. 1C is a block diagram showing components of the apparatus 100. As shown in FIG. 1A, the apparatus 100 comprises a magnetic sensor array 110 that includes a plurality of magnetic sensors 105, with four magnetic sensors 105A, 105B, 105C, and 105D shown. (For simplicity, this document refers generally to the magnetic sensors by the reference number 105. Individual magnetic sensors are given the reference number 105 followed by a letter.) The magnetic sensor array 110 in the exemplary embodiment of FIG. 1A is a linear array.

In some embodiments, each of the plurality of magnetic sensors 105 is coupled to at least one address line 120. (For simplicity, this document refers generally to the address lines by the reference number 120. Individual address lines are given the reference number 120 followed by a letter.) In the exemplary embodiment shown in FIG. 1A, each magnetic sensor 105 of the magnetic sensor array 110 is coupled to two address lines 120. Specifically, the magnetic sensor 105A is coupled to the address lines 120A and 120E, the magnetic sensor 105B is coupled to the address lines 120B and 120E, the magnetic sensor 105C is coupled to the address lines 120C and 120E, and the magnetic sensor 105D is coupled to the address lines 120D and 120E. The address lines 120A, 120B, 120C, and 120D reside under the magnetic sensors 105A, 105B, 105C, and 105D, respectively, and the address line 120E resides over the magnetic sensors 105. FIG. 1B shows the magnetic sensor 105D in relation to the address lines 120D and 120E.

The apparatus 100 also includes a fluid chamber 115 that is adjacent to the magnetic sensor array 110. As its name suggests, the fluid chamber 115 is configured to hold fluids when the apparatus 100 is in use. The fluid chamber 115 has a wall 117 that is adjacent to the magnetic sensor array 110. This wall 117 is referred to herein as a proximal wall. When the apparatus 100 is in use, the magnetic sensors 105 are able to detect, through the wall 117, magnetic labels (e.g., nanoparticles) that are in the fluid chamber 115. Thus, the wall 117 has properties and characteristics that protect the magnetic sensors 105 from whatever fluid is in the fluid chamber 115 while still allowing the magnetic sensors 105 to detect magnetic labels that are within the fluid chamber 115. For example, the material of the wall 117 (and possibly of the rest of the fluid chamber 115) may be or comprise an insulator. For example, in some embodiments, a surface of the wall 117 comprises polypropylene, gold, glass, or silicon. In addition, the thickness of the wall 117 is selected so that the magnetic sensors 105 can detect magnetic labels within the fluid chamber. In some embodiments, the proximal wall 117 is approximately 2 to 20 nm thick.

In some embodiments, the proximal wall 117 has a structure (or multiple structures) configured to anchor nucleic acid or a nucleic acid polymerase to the proximal wall 117. For example, the structure (or structures) may include a cavity or a ridge.

To simplify the explanation, FIGS. 1A and 1B illustrate an exemplary apparatus 100 with a single fluid chamber 115 and only four magnetic sensors 105A, 105B, 105C, 105D in the magnetic sensor array 110. It is to be appreciated that the apparatus 100 may have many more magnetic sensors 105 in the magnetic sensor array 110, and it may have either additional fluid chambers 115 or a more intricate single fluid chamber 115. In general, any configuration of magnetic sensors 105 and fluid chamber(s) 115 that allows the magnetic sensors 105 to detect magnetic labels in the fluid chamber(s) 115 may be used.

As an example of an apparatus with a larger number of magnetic sensors 105 in the magnetic sensor array 110, FIGS. 2A, 2B, 2C, and 2D illustrate portions of an exemplary apparatus 100 that includes several channels, each of which may be a separate fluid chamber 115, or the aggregation of which may be a single fluid chamber 115. In the embodiment of the apparatus 100 shown in FIGS. 2A, 2B, 2C, and 2D, the plurality of magnetic sensors 105 of the magnetic sensor array 110 is arranged in a rectangular grid pattern. Each of the address lines 120 identifies a row or a column of the magnetic sensor array 110. It is to be understood that FIGS. 2A, 2B, 2C, and 2D show only a portion of the apparatus 100 to avoid obscuring the parts of the apparatus 100 being discussed. It is to be understood that the various illustrated components (e.g., address lines 120, magnetic sensors 105, fluid channels 115, etc.) may not be visible in a physical instantiation of the apparatus 100 (e.g., they may be covered by protective material, such as an insulator).

Figure 2A:
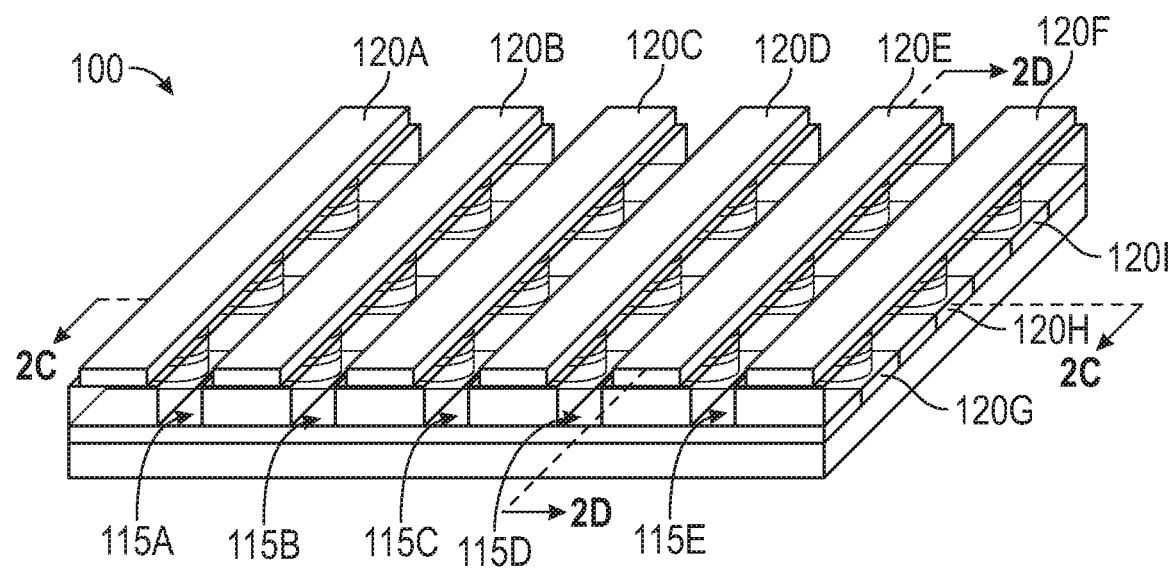
FIGS. 2A, 2B, 2C, and 2D illustrate an exemplary apparatus that includes several channels.

FIG. 2A is a perspective view of the exemplary apparatus 100. The apparatus 100 includes nine address lines 120, labeled as 120A, 120B, 120C, 120D, 120E, 120F, 120G, 120H, and 120I. It also includes fluid chambers 115A, 115B, 115C, 115D, and 115E. As explained above, the fluid chambers 115A, 115B, 115C, 115D, and 115E may be considered to be separate fluid chambers 115 or a single fluid chamber 115.

Figure 2B:
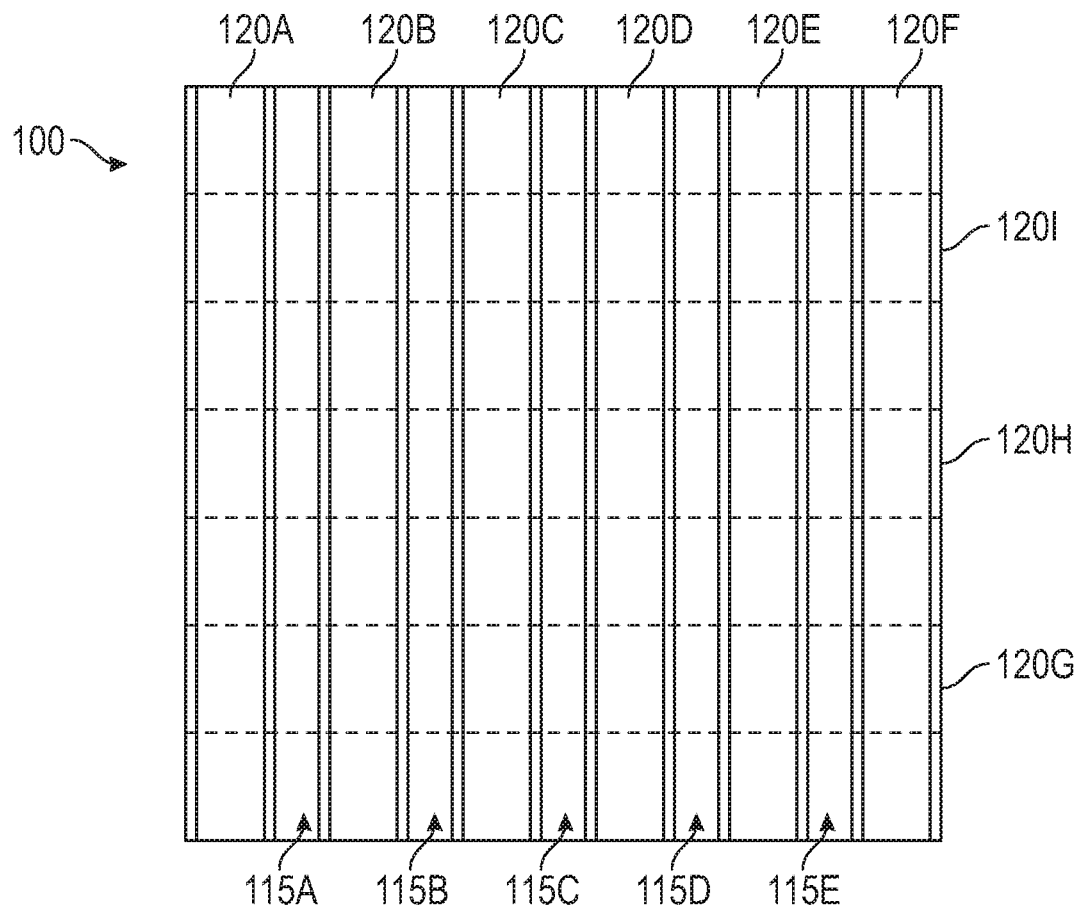

FIG. 2B is a top view of the exemplary apparatus 100 from FIG. 2A. The address lines 120G, 120H, and 120I, which are not visible from the top view, are shown using dashed lines to indicate their locations. The address lines 120A-120F are shown in solid lines but, as explained above, the address lines 120A-120F might also not be visible in the top view (e.g., they may be covered by protective material, such as an insulator).

Figure 2C:
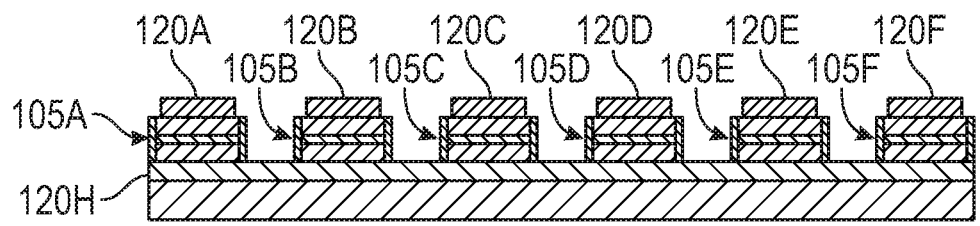

FIG. 2C is a cross-sectional view of the apparatus 100 along the line labeled "2C" in FIG. 2A. As shown, each of the address lines 120A, 120B, 120C, 120D, 120E, and 120F is in contact with the top of one of the magnetic sensors 105 along the cross-section (namely, address line 120A is in contact with magnetic sensor 105A, address line 120B is in contact with magnetic sensor 105B, address line 120C is in contact with magnetic sensor 105C, address line 120D is in contact with magnetic sensor 105D, address line 120E is in contact with magnetic sensor 105E, and address line 120F is in contact with magnetic sensor 105F). The address line 120H is in contact with the bottom of each of the magnetic sensors 105A, 105B, 105C, 105D, 105E, and 105F.

Figure 2D:
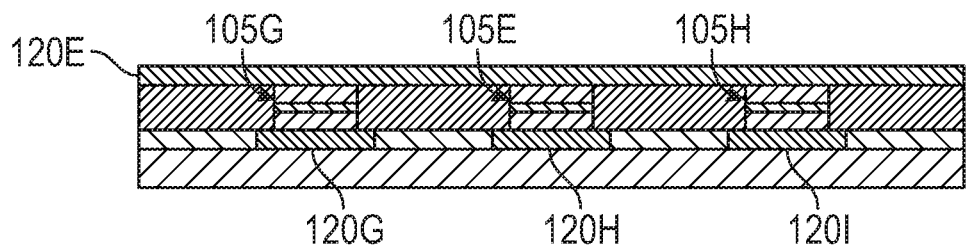

FIG. 2D is a cross-sectional view of the apparatus 100 along the line labeled "2D" in FIG. 2A. As shown, the address line 120E is in contact with the top of each of the sensors 105G, 105E, and 105H along the cross-section. Each of the address lines 120G, 120H, and 120I is in contact with the bottom of one of the magnetic sensors 105 along the cross-section (namely, address line 120G is in contact with magnetic sensor 105G, address line 120H is in contact with magnetic sensor 105E, and address line 120I is in contact with magnetic sensor 105H).

In some embodiments, each of the magnetic sensors 105 of the magnetic sensor array 110 is a thin film device that uses the magnetoresistance (MR) effect to detect magnetic labels in the fluid chamber 115. Each magnetic sensor 105 may operate as a potentiometer with a resistance that varies as the strength and/or direction of the sensed magnetic field changes. Each magnetic sensor 105 may have dimensions less than 30 nm to detect magnetic fields on the order of a few mT.

Figure 3:
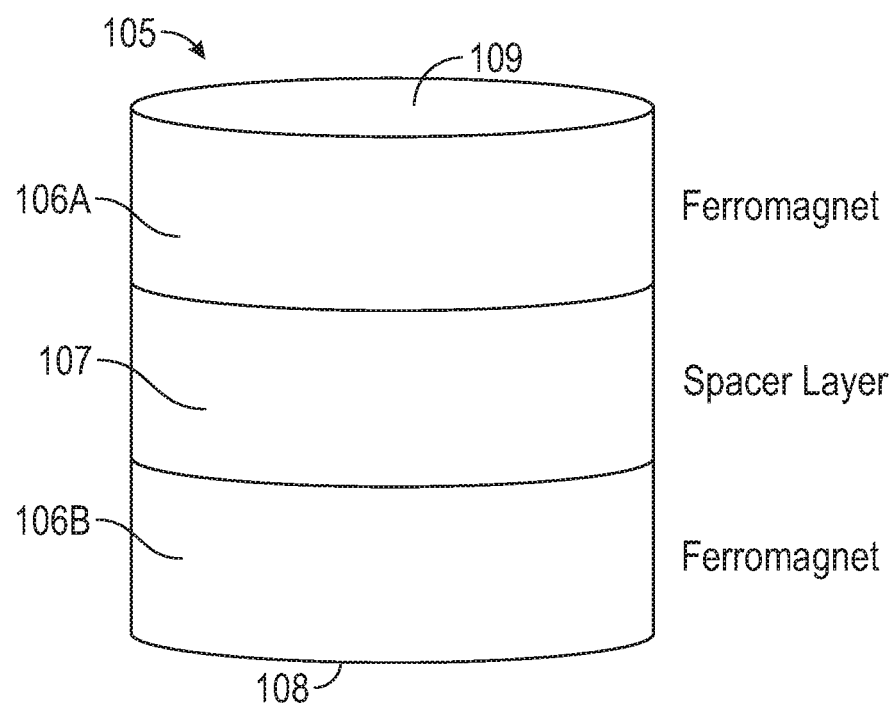
FIG. 3 illustrates a portion of a magnetic sensor in accordance with some embodiments.

FIG. 3 illustrates a portion of a magnetic sensor 105 in accordance with some embodiments. The exemplary magnetic sensor 105 of FIG. 3 has a bottom 108 and a top 109 and comprises three layers, e.g., two ferromagnetic layers 106A, 106B separated by a nonmagnetic spacer layer 107. The nonmagnetic spacer layer 107 may be, for example, a metallic material such as, for example, copper or silver, in which case the structure is called a spin valve (SV), or it may be an insulator such as, for example, alumina or magnesium oxide, in which case the structure is referred to as a magnetic tunnel junction (MTJ). Suitable materials for use in the ferromagnetic layers 106A, 106B include, for example, alloys of Co, Ni, and Fe (sometimes mixed with other elements). In some embodiments, the ferromagnetic layers 106A, 106B are engineered to have their magnetic moments oriented either in the plane of the film or perpendicular to the plane of the film. Additional materials may be deposited both below and above the three layers 106A, 106B, and 107 shown in FIG. 3 to serve purposes such as interface smoothing, texturing, and protection from processing used to pattern the apparatus 100, but the active region of the magnetic sensor 105 lies in this trilayer structure. Thus, a component that is in contact with a magnetic sensor 105 may be in contact with one of the three layers 106A, 106B, or 107, or it may be in contact with another part of the magnetic sensor 105.

Figure 4A:
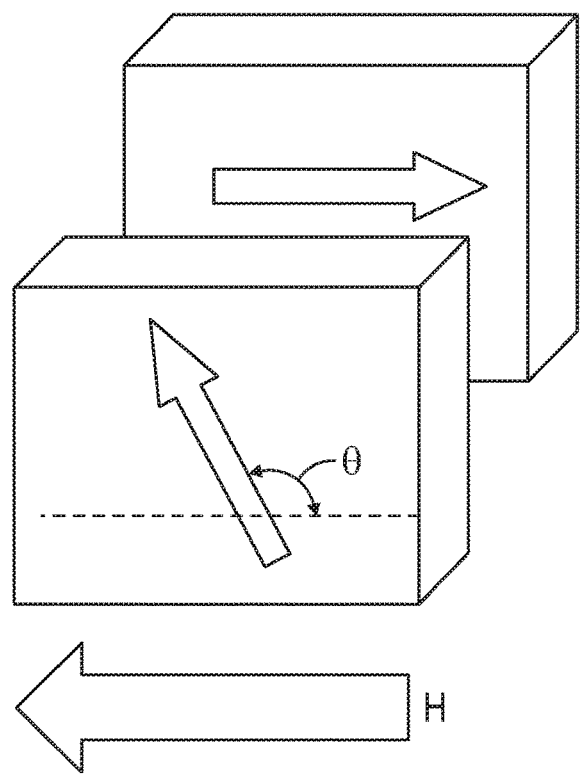
FIGS. 4A and 4B illustrate the relationship between the resistance of the exemplary sensor illustrated in FIG. 3 and the angle between the moments of its two ferromagnetic layers.
Figure 4B:
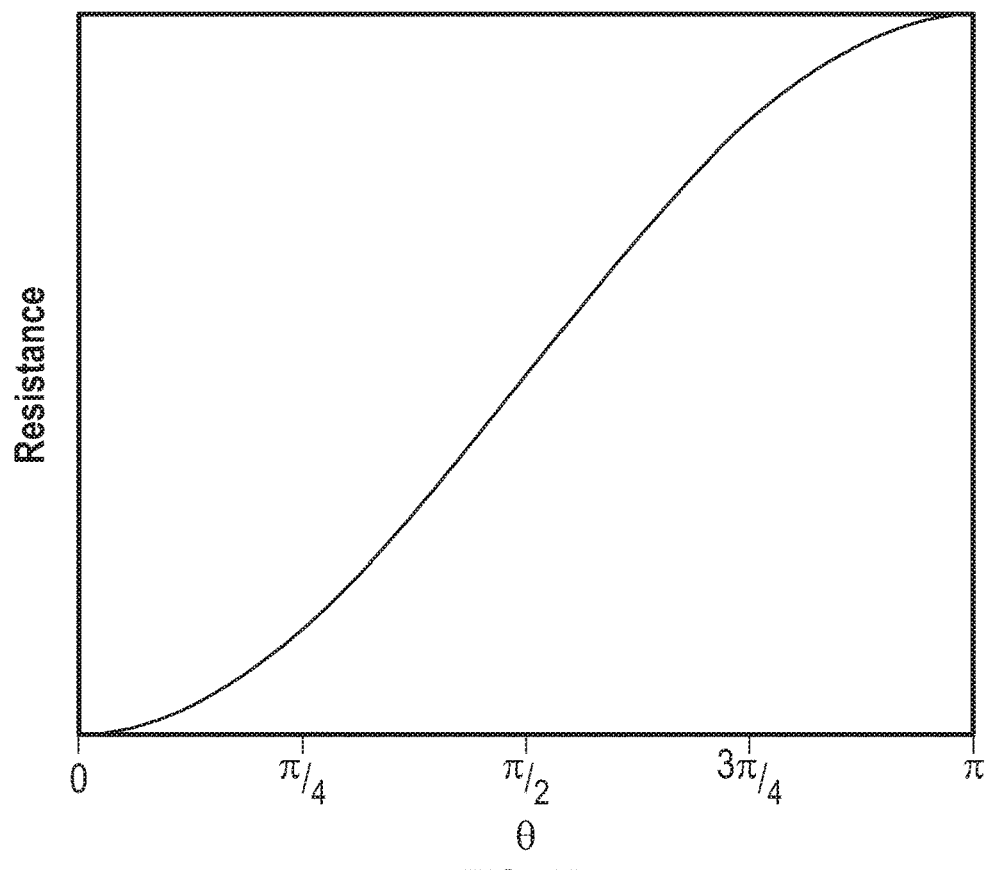

As shown in FIGS. 4A and 4B, the resistance of MR sensors is proportional to 1-cos(θ), where θ is the angle between the moments of the two ferromagnetic layers 106A, 106B shown in FIG. 3. To maximize the signal generated by a magnetic field and provide a linear response of the magnetic sensor 105 to an applied magnetic field, the magnetic sensor 105 may be designed such that the moments of the two ferromagnetic layers 106A, 106B are oriented π/2 or 90 degrees with respect to one another in the absence of a magnetic field. This orientation can be achieved by any number of methods that are known in the art. One solution is to use an antiferromagnet to "pin" the magnetization direction of one of the ferromagnetic layers (either 106A or 106B, designated as "FM1") through an effect called exchange biasing and then coat the sensor with a bilayer that has an insulating layer and permanent magnet. The insulating layer avoids electrical shorting of the magnetic sensor 105, and the permanent magnet supplies a "hard bias" magnetic field perpendicular to the pinned direction of FM1 that will then rotate the second ferromagnet (either 106B or 106A, designated as "FM2") and produce the desired configuration. Magnetic fields parallel to FM1 then rotate FM2 about this 90 degree configuration, and the change in resistance results in a voltage signal that can be calibrated to measure the field acting upon the magnetic sensor 105. In this manner, the magnetic sensor 105 acts as a magnetic-field-to-voltage transducer.

Note that although the example discussed immediately above described the use of ferromagnets that have their moments oriented in the plane of the film at 90 degrees with respect to one another, a perpendicular configuration can alternatively be achieved by orienting the moment of one of the ferromagnetic layers 106A, 106B out of the plane of the film, which may be accomplished using what is referred to as perpendicular magnetic anisotropy (PMA).

Figure 5A:
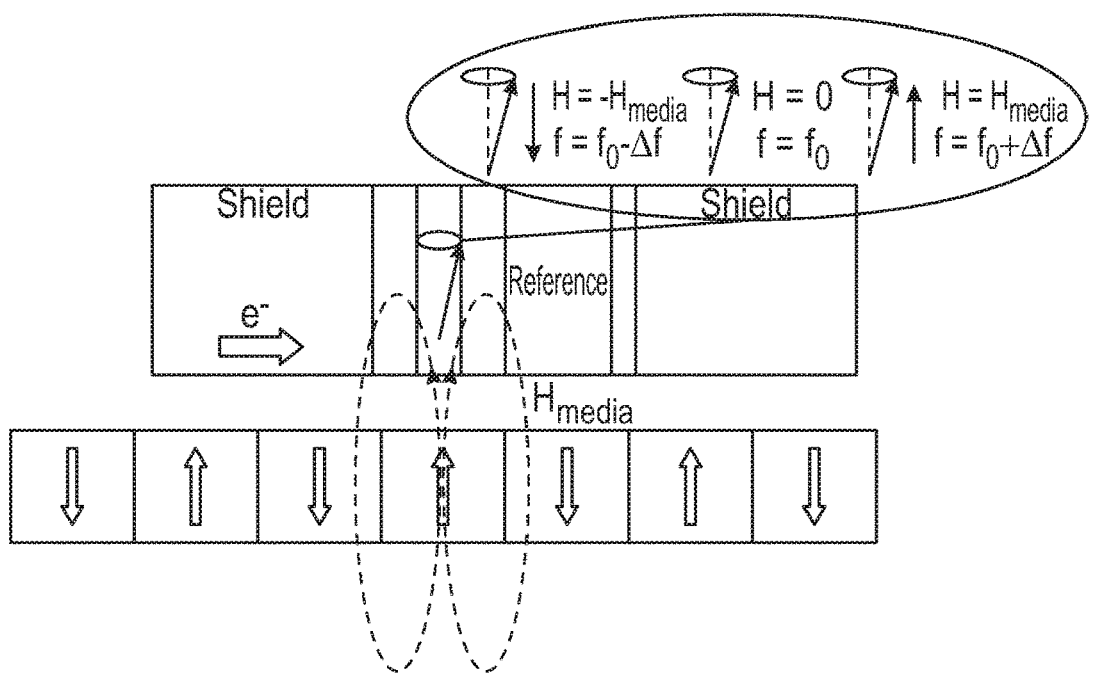
FIG. 5A illustrates the concept of using a spin torque oscillator (STO) sensor.
Figure 5B:
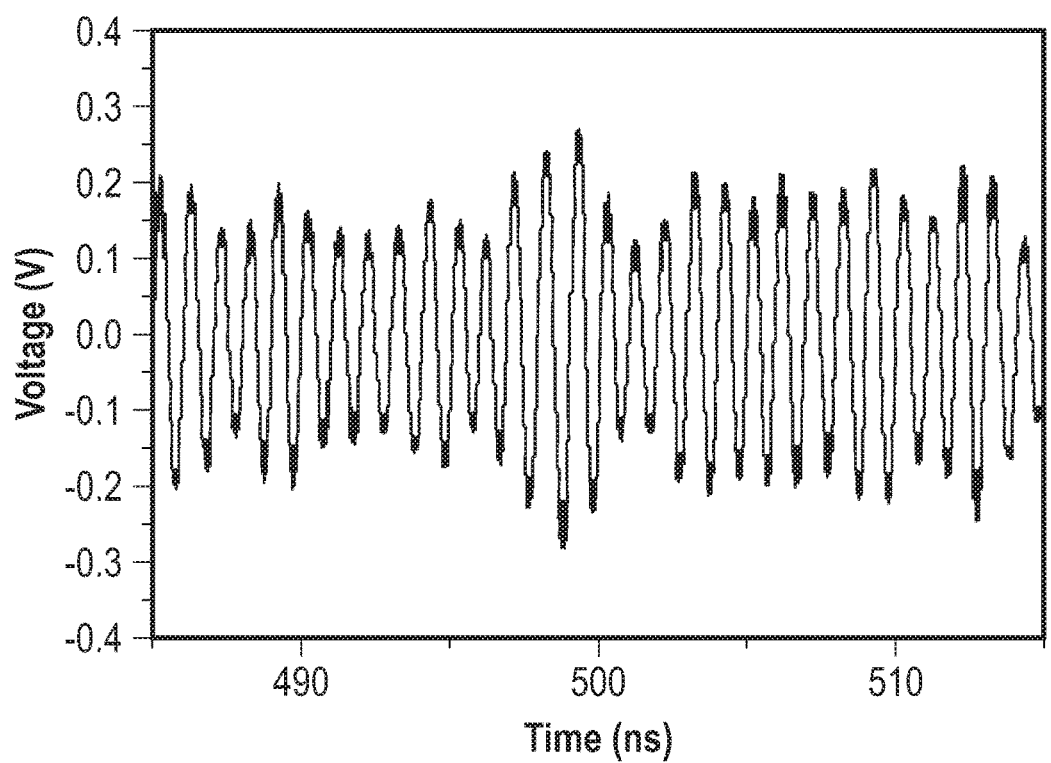
FIG. 5B shows the experimental response of an exemplary STO through a delay detection circuit.
Figure 5C:
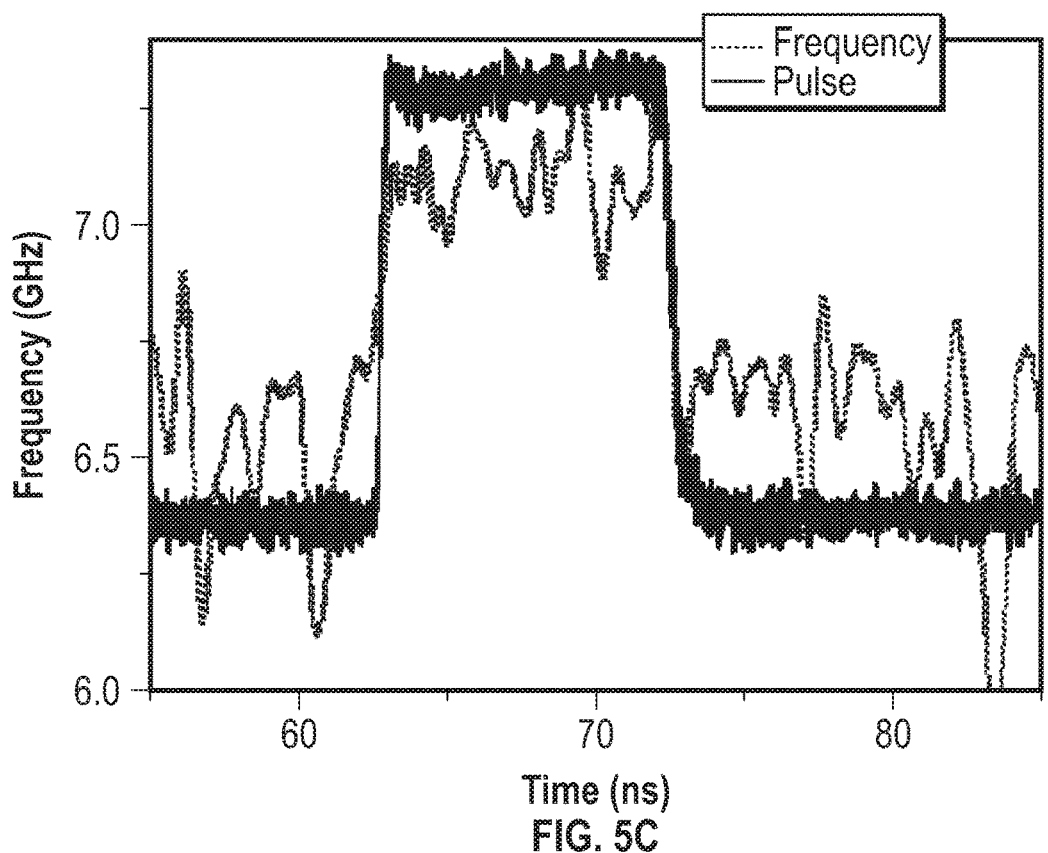
FIGS. 5C and 5D illustrate how STOs may be used as nanoscale magnetic field detectors in accordance with some embodiments.
Figure 5D:
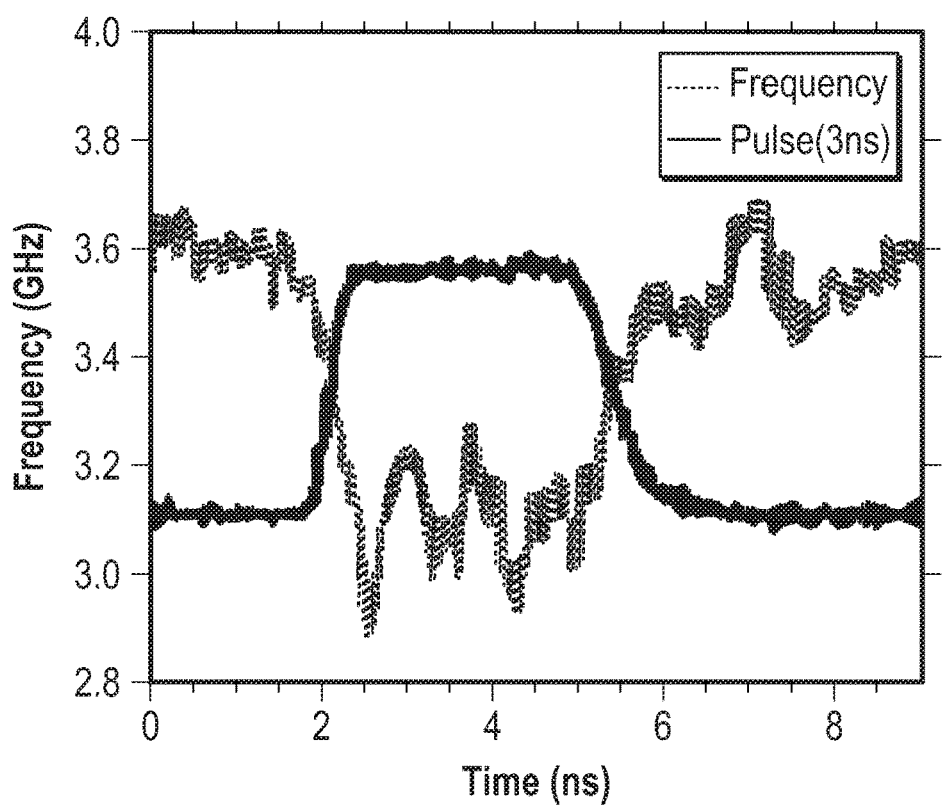

In some embodiments, the magnetic sensors 105 use a quantum mechanical effect known as spin transfer torque. In such devices, the electrical current passing through one ferromagnetic layer 106A (or 106B) in a SV or a MTJ preferentially allows electrons with spin parallel to the layer's moment to transmit through, while electrons with spin antiparallel are more likely to be reflected. In this manner, the electrical current becomes spin polarized, with more electrons of one spin type than the other. This spin-polarized current then interacts with the second ferromagnetic layer 106B (or 106A), exerting a torque on the layer's moment. This torque can in different circumstances either cause the moment of the second ferromagnetic layer 106B (or 106A) to precess around the effective magnetic field acting upon the ferromagnet, or it can cause the moment to reversibly switch between two orientations defined by a uniaxial anisotropy induced in the system. The resulting spin torque oscillators (STOs) are frequency-tunable by changing the magnetic field acting upon them. Thus, they have the capability to act as magnetic-field-to-frequency (or phase) transducers, as is shown in FIG. 5A, which illustrates the concept of using a STO sensor. FIG. 5B shows the experimental response of a STO through a delay detection circuit when an AC magnetic field with a frequency of 1 GHz and a peak-to-peak amplitude of 5 mT is applied across the STO. This result and those shown in FIGS. 5C and 5D for short nanosecond field pulses illustrate how these oscillators may be used as nanoscale magnetic field detectors. Further details may be found in T. Nagasawa, H. Suto, K. Kudo, T. Yang, K. Mizushima, and R. Sato, "Delay detection of frequency modulation signal from a spin-torque oscillator under a nanosecond-pulsed magnetic field," Journal of Applied Physics, Vol. 111, 07C908 (2012).

As illustrated in FIG. 1C, in some embodiments, the apparatus 100 includes sensing circuitry 130 coupled to the magnetic sensor array 110 via the address lines 120. In operation, the sensing circuitry 130 applies a current to the address lines 120 to detect a characteristic of at least one of the plurality of magnetic sensors 105 in the magnetic sensor array 110, where the characteristic indicates a presence or an absence of a magnetically-labeled nucleotide precursor in the fluid chamber 115. For example, in some embodiments, the characteristic is a magnetic field or a resistance, or a change in magnetic field or a change in resistance. In some embodiments, the characteristic is a noise level. In some embodiments, the magnetic sensor comprises a magnetic oscillator, and the characteristic is a frequency of a signal associated with or generated by the magnetic oscillator.

Figure 6A:
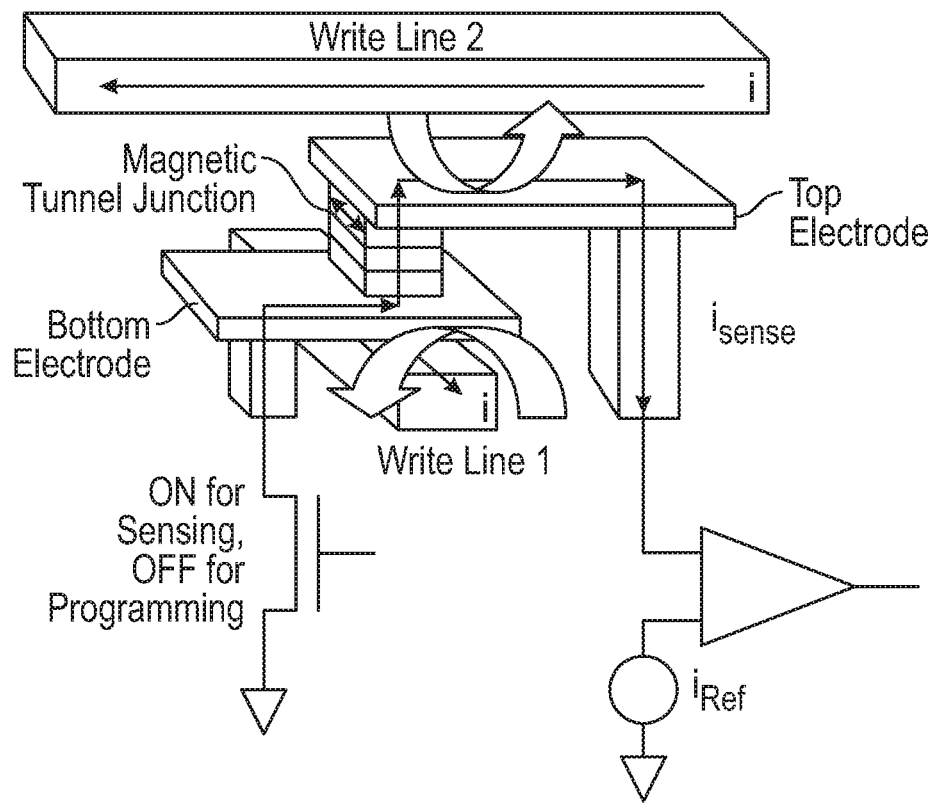
FIGS. 6A and 6B illustrate two selector element approaches in accordance with some embodiments.
Figure 6B:
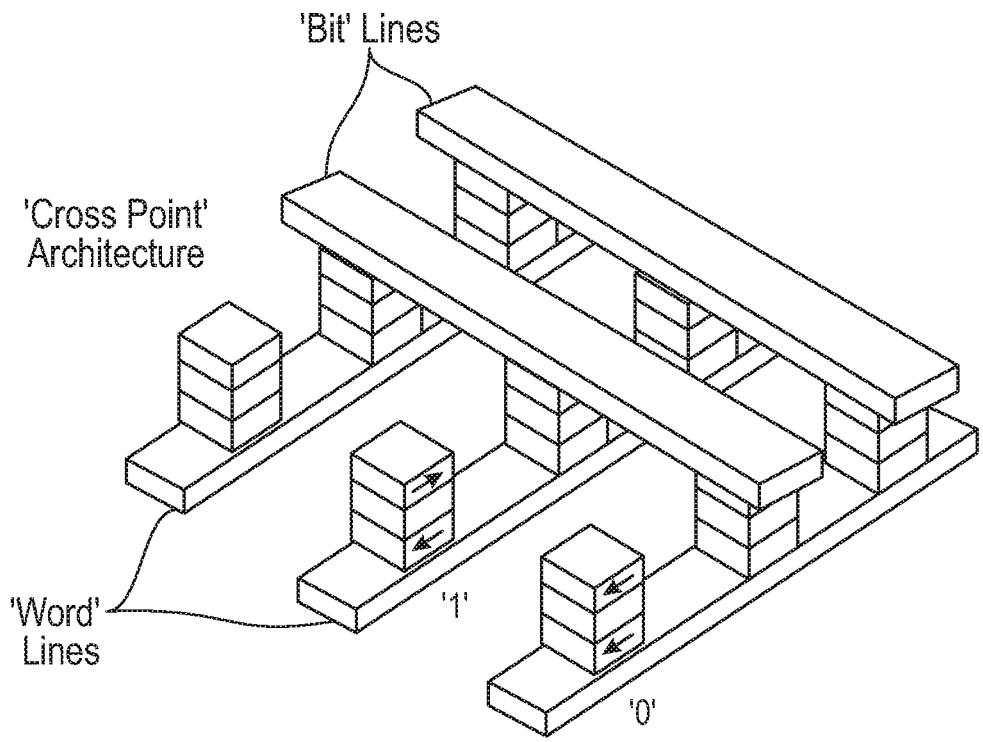

In some embodiments, the magnetic sensor array 110 includes a selector element that reduces the chances of "sneak" currents that could transmit through neighboring elements and degrade the performance of the magnetic sensor array 110. FIGS. 6A and 6B illustrate two approaches in accordance with some embodiments. In FIG. 6A, a CMOS transistor is coupled in series with the magnetic sensor 105. For more detail on the configuration shown in FIG. 6A, see B. N. Engel, J. Akerman, B. Butcher, R. W. Dave, M. DeHerrera, M. Durlam, G. Grynkewich, J. Janesky, S. V. Pietambaram, N. D. Rizzo, J. M. Slaughter, K. Smith, J. J. Sun, and S. Tehrani, "A 4-Mb Toggle MRAM Based on a Novel Bit and Switching Method," IEEE Transactions on Magnetics, Vol. 41, 132 (2005).

In FIG. 6B, a diode or a diode-like element is deposited together with the magnetic films and then placed into a "cross-point" architecture, where CMOS transistors at the periphery of the magnetic sensor array 110 turn on the individual addressing lines 120 (e.g., word and bit lines) to address individual magnetic sensors 105 in the array. The use of CMOS select transistors may be simpler due to the prevalence of foundries available to fabricate the front end (i.e., all the nanofabrication to build the CMOS transistors and underlying circuitry), but the types of currents required for operation may require a cross-point design to eventually reach the densities required of the magnetic sensor array 110. Additional details on the configuration shown in FIG. 6B may be found in C. Chappert, A. Fert, and F. N. Van Daul, "The emergence of spin electronics in data storage," Nature Materials, Vol. 6, 813 (2007).

In nucleic acid sequencing applications, it may be difficult or impossible to orient the moments of each of the magnetic labels (e.g., nanoparticles) in the same direction, as the position of each label with respect to a magnetic sensor 105 as well as the axis of the label's magnetic moment can vary. Moreover, to achieve high densities of magnetic sensors 105 in the magnetic sensor array 110, the magnetic labels may need to be on the order of tens of nanometers, in which case the magnetic labels are likely to be superparamagnetic, meaning that they maintain a measurable moment without a defined axis for the moment to point (i.e., the magnetic field acting on a magnetic sensor 105 would fluctuate in time in its direction). These challenges can increase the difficulty of accurate detection.

Detection can be performed in a variety of ways. To achieve high-throughput sequencing relying on each magnetic sensor 105 being capable of detecting a single magnetic label (e.g., a nanoparticle), the magnetic labels should be small, ideally comparable to the size of an individual magnetic sensor 105. This can be achieved with a variety of magnetic labels that can be readily synthesized as is known in the art. For example, the magnetic labels may be nanoparticles with high magnetic anisotropy. Examples of nanoparticles with high magnetic anisotropy include, but are not limited to, $Fe_3O_4$, FePt, FePd, and CoPt. To facilitate chemical binding to nucleotides, the particles may be synthesized and coated with $SiO_2$. See, e.g., M. Aslam, L. Fu, S. Li, and V. P. Dravid, "Silica encapsulation and magnetic properties of FePt nanoparticles," Journal of Colloid and Interface Science, Volume 290, Issue 2, 15 Oct. 2005, pp. 444-449.

Because magnetic labels of this size have permanent magnetic moments whose direction fluctuates randomly on very short time scales, some embodiments rely on sensitive sensing schemes that detect fluctuations in magnetic field caused by the presence of the magnetic labels.

In some embodiments, the sensing circuitry 130 detects deviations or fluctuations in the magnetic environment of some or all of the magnetic sensors 105 in the magnetic sensor array 110. For example, a magnetic sensor 105 of the MR type in the absence of a magnetic label should have relatively small noise above a certain frequency as compared to a magnetic sensor 105 in the presence of a magnetic label, because the field fluctuations from the magnetic label will cause fluctuations of the moment of the sensing ferromagnet. These fluctuations can be measured using heterodyne detection (e.g., by measuring noise power density) or by directly measuring the voltage of the magnetic sensor 105 and evaluated using a comparator circuit to compare to a dummy sensor element that does not sense the fluid chamber 115. In the case the magnetic sensors 105 include STO elements, fluctuating magnetic fields from magnetic labels would cause jumps in phase for the magnetic sensors due to instantaneous changes in frequency, which can be detected using a phase detection circuit. Another option is to design the STO such that it oscillates only within a small magnetic field range such that the presence of a magnetic label would turn off the oscillations. One advantage of the array design shown in FIG. 2A is that multiple magnetic sensors 105 (e.g., nominally to the left and right of a magnetic label) can be used in post-processing of data to improve the accuracy of magnetic label detection.

In some embodiments, the apparatus 100 is fabricated using photolithographic processes and thin film deposition.

Figure 7:
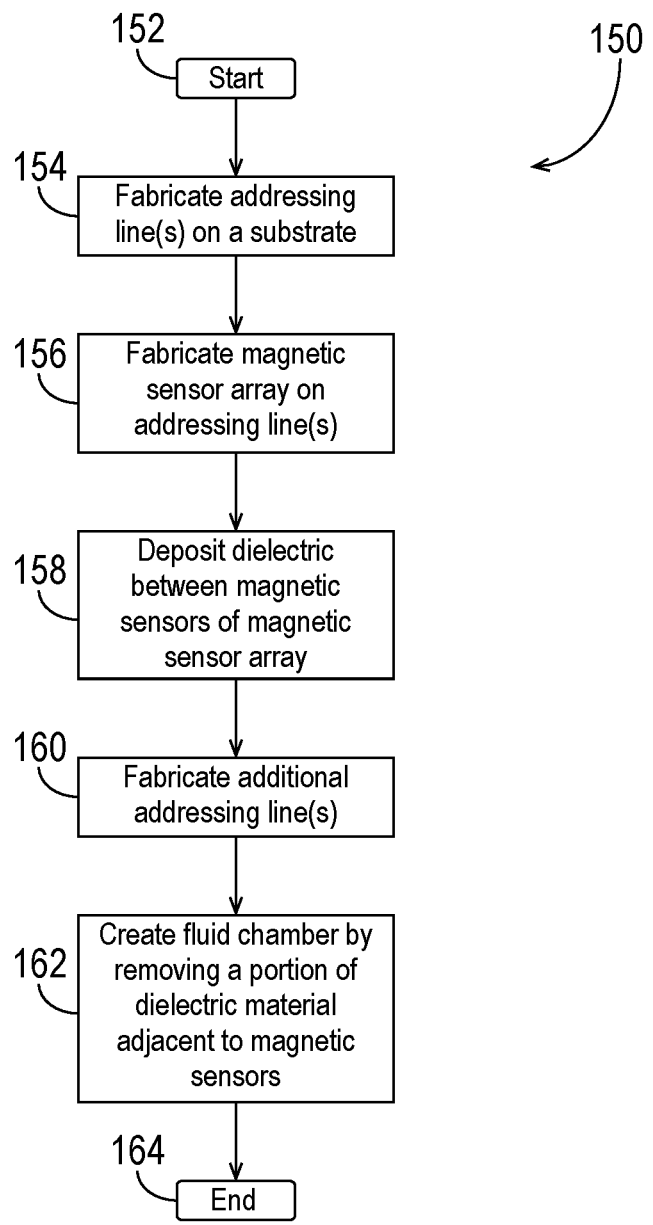
FIG. 7 is a flowchart illustrating a method of manufacturing an apparatus for nucleic acid sequencing in accordance with some embodiments.
Figure 8:
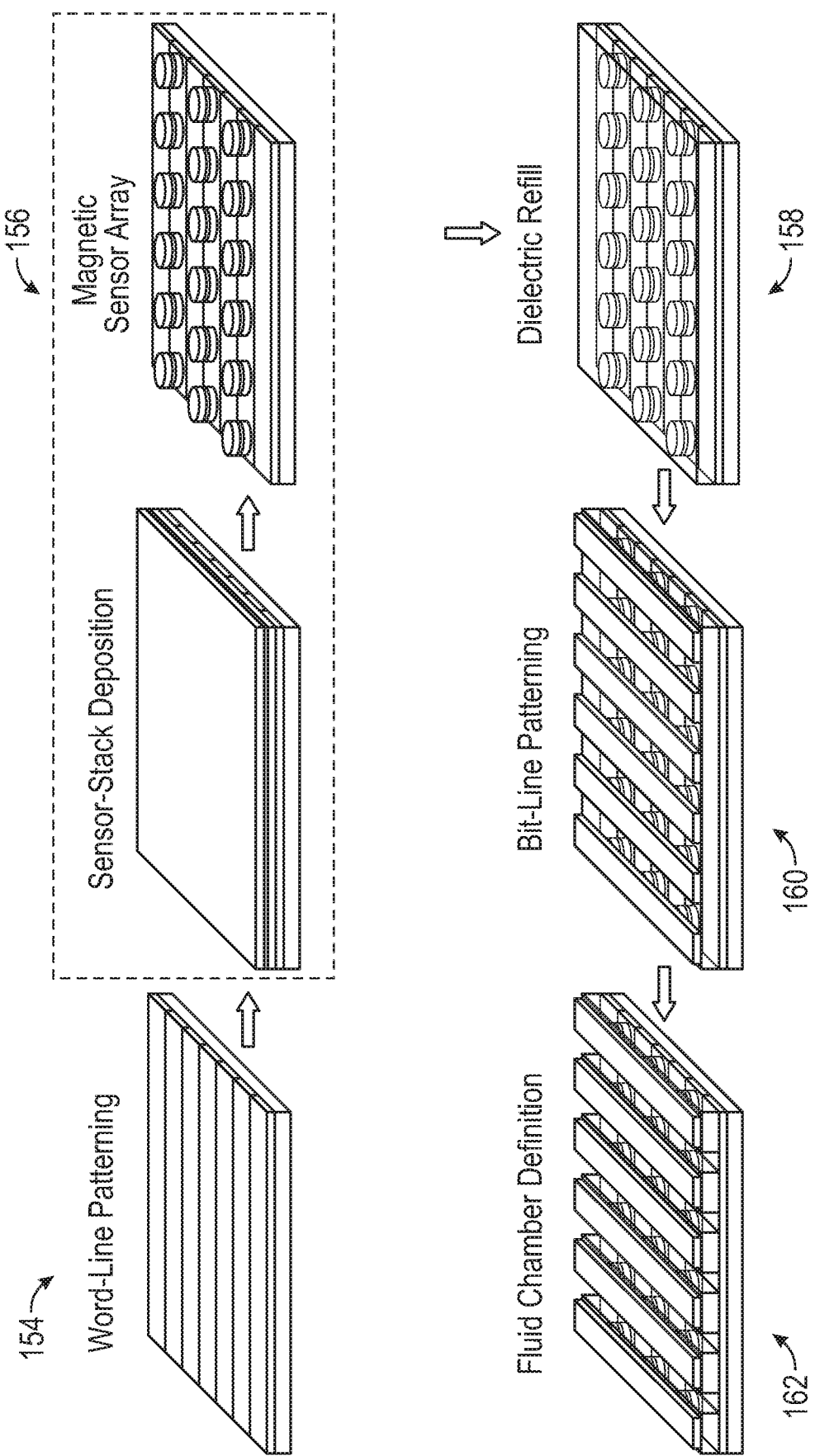
FIG. 8 illustrates the results of each step of the method of manufacturing illustrated in FIG. 7.
Figure 9A:
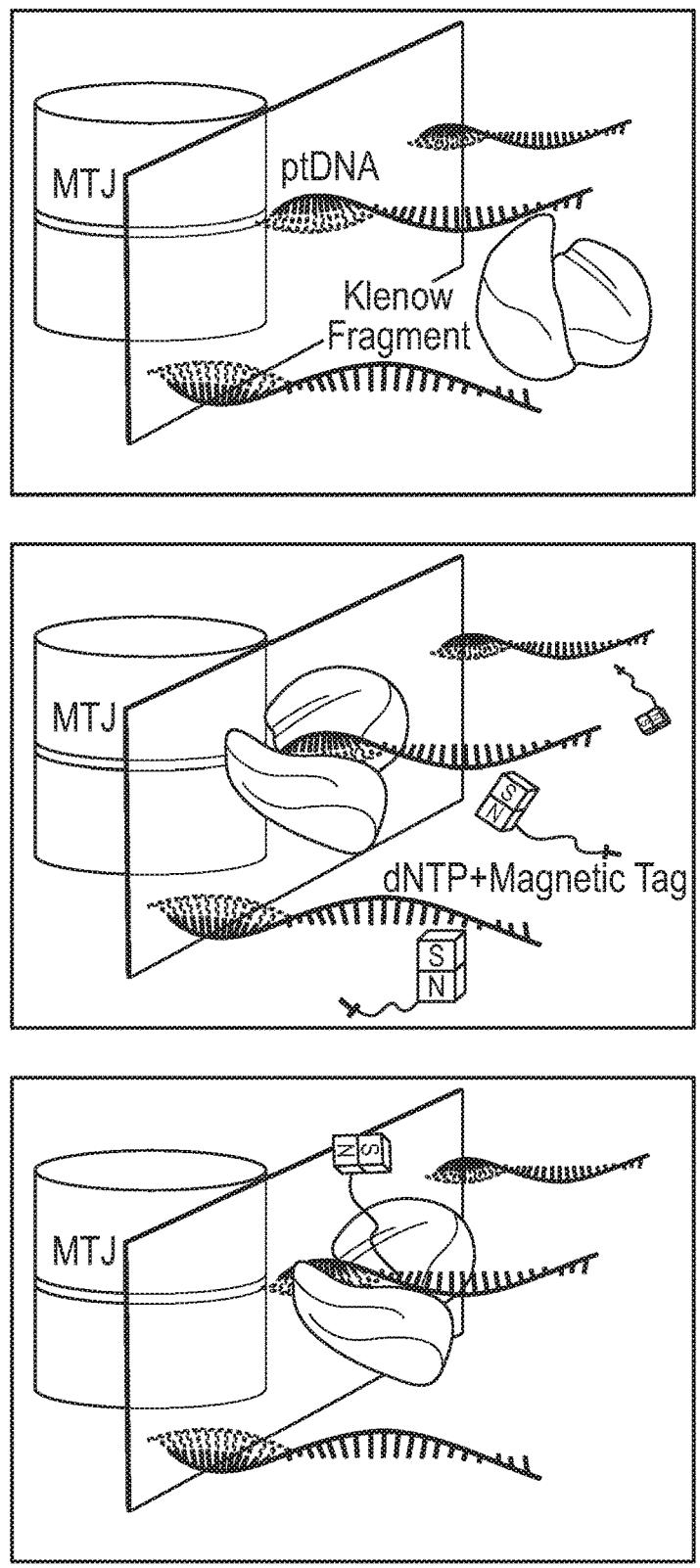
FIG. 9A illustrates static SBS in accordance with some embodiments.
Figure 9B:
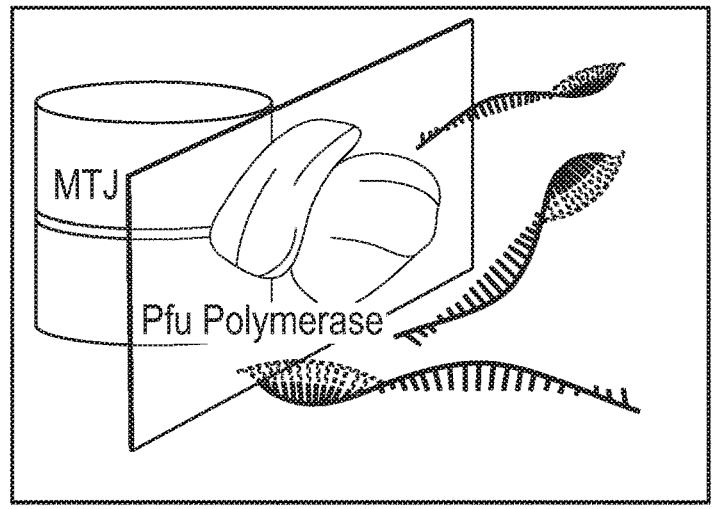
FIG. 9B illustrates dynamic SBS in accordance with some embodiments.
Figure 9B:
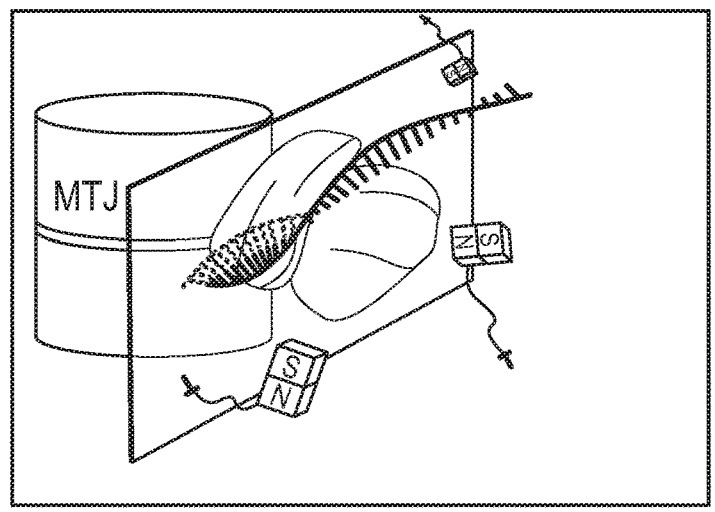
Figure 9B:
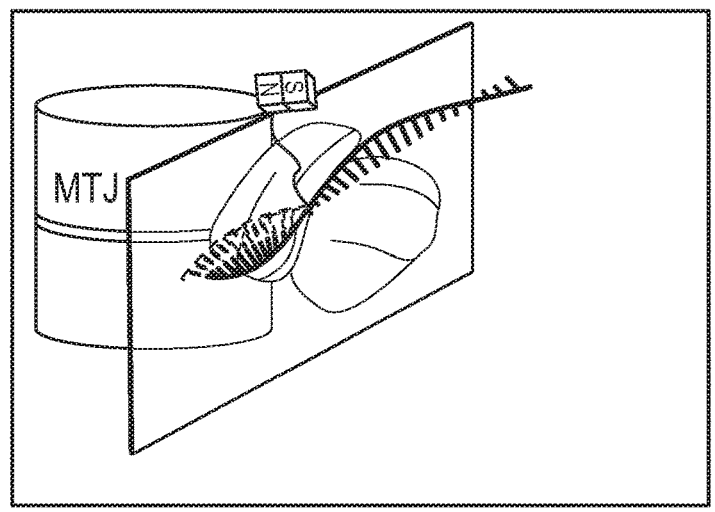

FIG. 7 illustrates a method 150 of manufacturing the apparatus 100, and FIG. 8 illustrates the results of each step of the fabrication process 150. At 152, the method begins. At 154, at least one addressing line 120 is fabricated on a substrate, for example, by depositing. At 156, the magnetic sensor array 110 is fabricated on the at least one addressing line 120. Each magnetic sensor 105 of the magnetic sensor array 110 has a bottom portion 108 and a top portion 109. (See FIG. 3.) The bottom portion 108 is coupled to the at least one addressing line 120. In some embodiments, the bottom portion 108 of each magnetic sensor 105 is in contact with the at least one addressing line 120.

At 158, dielectric material is deposited between the magnetic sensors 105 of the magnetic sensor array 110.

At 160, additional addressing lines 120 are fabricated. Each of these additional addressing lines is coupled to the top portion 109 of at least one magnetic sensor 105 in the magnetic sensor array 110. In some embodiments, the top portion 109 of each magnetic sensor 105 is in contact with an addressing line 120. In some embodiments, the bottom portion 108 of a magnetic sensor 105 is in contact with a first addressing line 120A, and the top portion 109 of the magnetic sensor 105 is in contact with a second addressing line 120B.

At 162, a portion of the dielectric material adjacent to the magnetic sensors 105 is removed (e.g., by milling, etching, or any other suitable removal process) to create the fluid chamber 115.

Methods of using embodiments of the apparatus 100 described above rely on the use of magnetically-labeled nucleotide precursors comprising cleavable magnetic labels. These cleavable magnetic labels may comprise, for example, a magnetic nanoparticle, such as, for example, a molecule, a superparamagnetic nanoparticle, or a ferromagnetic particle.

There are a number of ways to attach and cleave the magnetic labels. For example, the magnetic labels may be attached to a base, in which case they may be cleaved chemically. As another example, the magnetic labels may be attached to a phosphate, in which case they may be cleaved by polymerase or, if attached via a linker, by cleaving the linker.

In some embodiments, the magnetic label is linked to the nitrogenous base (A, C, T, G, or a derivative) of the nucleotide precursor. After incorporation of the nucleotide precursor and the detection by the apparatus 100 (i.e., using the magnetic sensor array 110), the magnetic label is cleaved from the incorporated nucleotide.

In some embodiments, the magnetic label is attached via a cleavable linker. Cleavable linkers are known in the art and have been described, e.g., in U.S. Pat. Nos. 7,057,026, 7,414,116 and continuations and improvements thereof. In some embodiments, the magnetic label is attached to the 5-position in pyrimidines or the 7-position in purines via a linker comprising an allyl or azido group. In other embodiments, the linker comprises a disulfide, indole or a Sieber group. The linker may further contain one or more substituents selected from alkyl $(C_{1-6})$ or alkoxy $(C_{1-6})$, nitro, cyano, fluoro groups or groups with similar properties. Briefly, the linker can be cleaved by water-soluble phosphines or phosphine-based transition metal-containing catalysts. Other linkers and linker cleavage mechanisms are known in the art. For example, linkers comprising trityl, p-alkoxybenzyl esters and p-alkoxybenzyl amides and tert-butyloxycarbonyl (Boc) groups and the acetal system can be cleaved under acidic conditions by a proton-releasing cleavage agent. A thioacetal or other sulfur-containing linker can be cleaved using a thiophilic metals, such as nickel, silver or mercury. The cleavage protecting groups can also be considered for the preparation of suitable linker molecules. Ester- and disulfide containing linkers can be cleaved under reductive conditions. Linkers containing triisopropyl silane (TIPS) or t-butyldimethyl silane (TBDMS) can be cleaved in the presence of F ions. Photocleavable linkers cleaved by a wavelength that does not affect other components of the reaction mixture include linkers comprising O-nitrobenzyl groups. Linkers comprising benzyloxycarbonyl groups can be cleaved by Pd-based catalysts.

In some embodiments, the nucleotide precursor comprises a label attached to a polyphosphate moiety as described in, e.g., U.S. Pat. Nos. 7,405,281 and 8,058,031. Briefly, the nucleotide precursor comprises a nucleoside moiety and a chain of 3 or more phosphate groups where one or more of the oxygen atoms are optionally substituted, e.g., with S. The label may be attached to the $\alpha$, $\beta$, $\gamma$ or higher phosphate group (if present) directly or via a linker. In some embodiments, the label is attached to a phosphate group via a non-covalent linker as described, e.g., in U.S. Pat. No. 8,252,910. In some embodiments, the linker is a hydrocarbon selected from substituted or unsubstituted alkyl, substituted or unsubstituted heteroalkyl, substituted or unsubstituted aryl, substituted or unsubstituted heteroaryl, substituted or unsubstituted cycloalkyl, and substituted or unsubstituted heterocycloalkyl; see, e.g., U.S. Pat. No. 8,367,813. The linker may also comprise a nucleic acid strand; see, e.g., U.S. Pat. No. 9,464,107.

In embodiments in which the magnetic label is linked to a phosphate group, the nucleotide precursor is incorporated into the nascent chain by the nucleic acid polymerase, which also cleaves and releases the detectable magnetic label. In some embodiments, the magnetic label is removed by cleaving the linker, e.g., as described in U.S. Pat. No. 9,587,275.

In some embodiments, the nucleotide precursors are non-extendable "terminator" nucleotides, i.e., the nucleotides that have a 3'-end blocked from addition of the next nucleotide by a blocking "terminator" group. The blocking groups are reversible terminators that can be removed in order to continue the strand synthesis process as described herein. Attaching removable blocking groups to nucleotide precursors is known in the art. See, e.g., U.S. Pat. Nos. 7,541,444, 8,071,739 and continuations and improvements thereof. Briefly, the blocking group may comprise an allyl group that can be cleaved by reacting in aqueous solution with a metal-allyl complex in the presence of phosphine or nitrogen-phosphine ligands. Other examples of reversible terminator nucleotides used in sequencing by synthesis include the modified nucleotides described in U.S. Provisional App. Ser. No. 62/781,638 filed on Dec. 19, 2018 and entitled "3'-Protected Nucleotides," which is hereby incorporated by reference in its entirety for all purposes.

Methods of Sequencing

There are at least two classes of methods of performing nucleic acid sequencing using embodiments of the apparatus 100 described above. Two of these classes are referred to herein as "static SBS" and "dynamic SBS." In static SBS, nucleic acid is sequenced using immobilized nucleic acid strands that are tethered to the apparatus 100 in the proximity of the magnetic sensors 105 of the magnetic sensor array 110. In dynamic SBS, nucleic acid (e.g., DNA) can be sequenced using immobilized polymerase molecules that are tethered to the apparatus 100 in the proximity of the magnetic sensors 105 of the magnetic sensor array 110.

FIG. 9 is a high-level illustration of the two approaches. FIG. 9A illustrates static SBS, and FIG. 9B illustrates dynamic SBS. Both approaches are described below in more detail.

In static SBS, nucleic acid (e.g., DNA) can be sequenced using immobilized nucleic acid strands that are tethered to the apparatus 100 in the proximity of the magnetic sensors 105 of the magnetic sensor array 110. Four types of reversible terminator bases (RT-bases) are then added, either together or one at a time, and non-incorporated nucleotides are washed away. Then the magnetic labels, along with the terminal 3' blocker, are chemically removed from the nucleic acid strands before the next cycle begins.

The nucleic acid strands can be prepared in any suitable manner. For example, the nucleic acid strands can be prepared by random fragmentation of a nucleic acid sample, followed by 5' and 3' adapter ligation. These strands of the nucleic acid may then be captured on oligos bound or attached to the proximal wall 117 of the fluid chamber 115. Linear or exponential amplification including bridge amplification may be used to amplify each strand prior to sequencing.

To sequence the nucleic acid strands, magnetically-labeled nucleotide precursors may be introduced one at a time or all at once, as described below.

In some static SBS embodiments, magnetically-labeled nucleotide precursors are introduced one at a time. In such embodiments, the same magnetic label can be used for all of the nucleotide precursors. It is to be understood that as used herein, the phrase "the same magnetic label" does not refer to the same physical instance of a single magnetic label (i.e., it does not mean that a particular instance of a physical label is reused); instead, it refers to multiple physical instantiations of magnetic labels, all of which have identical characteristics or properties that render individual instances of them indistinguishable from one another. In contrast, the phrase "different magnetic labels" refers to magnetic labels that, either individually or as a group, have different characteristics or properties that allow them to be distinguished from other magnetic labels, whether individually or as a group.

In the disclosed static SBS embodiments, the nucleic acid strands are extended one nucleotide at a time, and the magnetic sensor array 110 is used to identify the bound magnetically-labeled nucleotide precursor.

Figure 10:
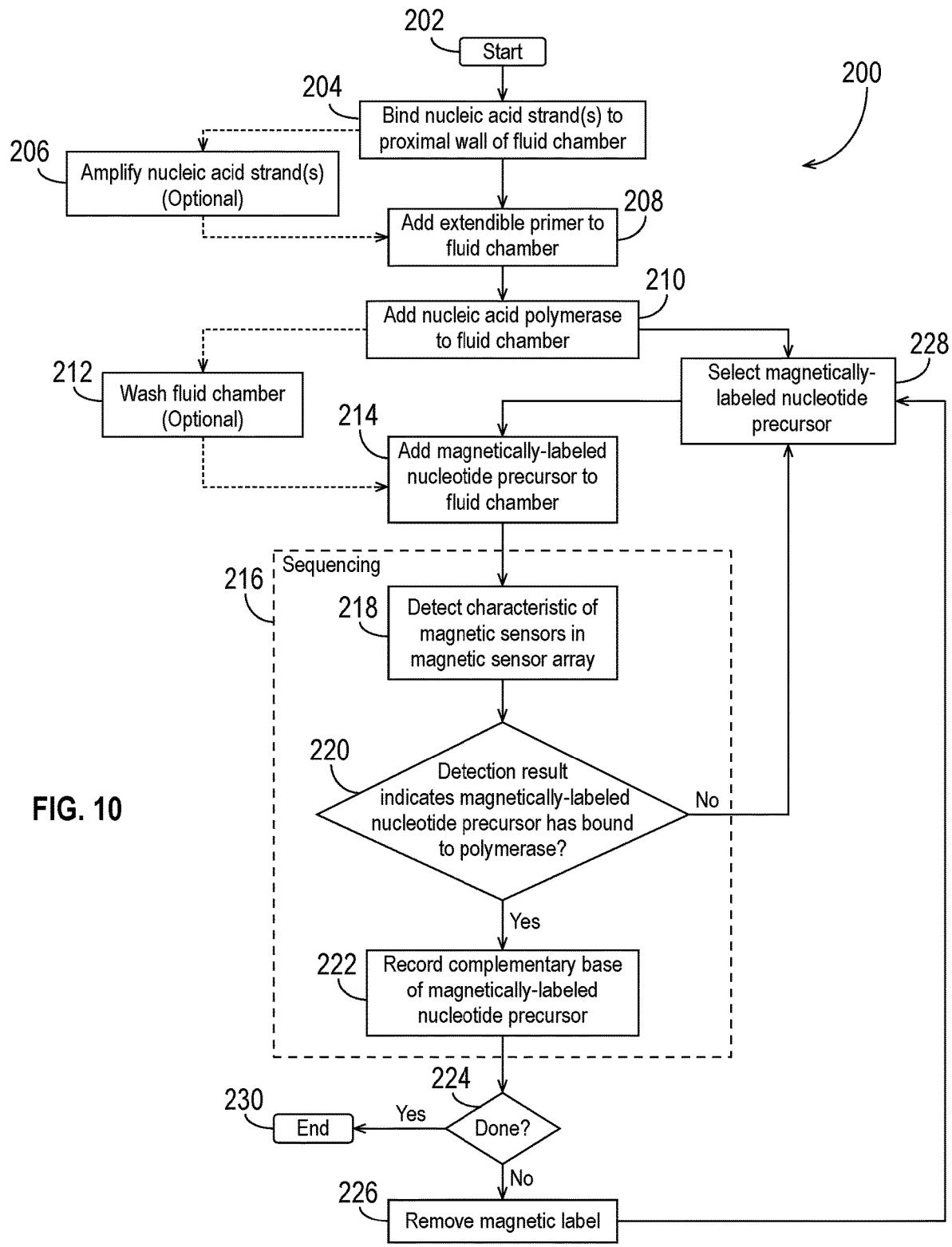
FIG. 10 is a flowchart illustrating a method of static SBS in accordance with some embodiments.

FIG. 10 is a flowchart illustrating a method 200 of static SBS in accordance with some embodiments, and FIGS. 11A, 11B, 11C, 11D, 11E, and 11F illustrate the method 200 graphically. At 202, the method begins. At 204, one or more nucleic acid strands are bound to the proximal wall 117 of the sequencing apparatus 100, as described above. There are a number of ways to bind the one or more nucleic acid strands to the proximal wall 117. For example, the nucleic acid strand may be bound to the proximal wall 117 by attaching an adapter to an end of the nucleic acid strand and coupling an oligonucleotide to the proximal wall 117 of the fluid chamber 115, wherein the oligonucleotide is complementary to the adapter. As another example, the nucleic acid strand may be bound to the proximal wall 117 by attaching the nucleic acid strand to the proximal wall 117 using a polystyrene or a polyacrylamide gel. As yet another example, the nucleic acid strand may be bound to the proximal wall 117 by immobilizing the nucleic acid strand via irreversible passive adsorption or affinity between molecules. In some embodiments, the proximal wall 117 comprises a cavity or a ridge, as described above, and binding the nucleic acid strand to the proximal wall comprises applying a hydrogel to the cavity or to the ridge.

At optional step 206, the nucleic acid strand(s) may be amplified using any suitable method, such as, for example, by leveraging the polymerase chain reaction (PCR) or linear amplification.

At 208, an extendible primer is added to the fluid chamber 115.

At 210, a nucleic acid polymerase is added to the fluid chamber 115. The nucleic acid polymerase may be any suitable nucleic acid polymerase. Desired characteristics of a nucleic acid polymerase (such as a DNA polymerase) that finds use in nucleic acid sequencing include one or more of the following: fast association rate for nucleic acid template and for nucleotide precursors or slow dissociation rate for nucleic acid template and for nucleotide precursors (association and dissociation rates being kinetic characteristics of a nucleic acid polymerase under a defined set of reaction conditions); high fidelity, low or undetectable exonuclease activity, including low or undetectable 3'-5' exonuclease (proofreading) activity or low or undetectable 5'-3' exonuclease activity; effective DNA strand displacement, high stability, high processivity (including long read length), salt tolerance and ability to incorporate modified nucleotide precursors including the precursors described herein.

Some examples of a suitable polymerase include B-family (Type B) polymerases lacking the 3'-5' exonuclease activity.

In some embodiments, the polymerase is a thermostable polymerase. Thermostable nucleic acid polymerases include *Thermus aquaticus* Taq DNA polymerase, *Thermus* sp. Z05 polymerase, *Thermus flavus* polymerase, *Thermotoga maritima* polymerases, such as TMA-25 and TMA-30 polymerases, Tth DNA polymerase, *Pyrococcus furiosus* (Pfu), *Pyrococcus woesei* (Pwo), *Thermatoga maritima* (Tma) and *Thermococcus Litoralis* (Tli or Vent) and the like.

In some embodiments, the polymerase lacks detectable 5'-3' exonuclease activity. Examples of DNA polymerases substantially lacking 5' to 3' nuclease activity include the Klenow fragment of *E. coli* DNA polymerase I; a *Thermus aquaticus* DNA polymerase (Taq) lacking the N-terminal 235 amino acids ("Stoffel fragment"), See U.S. Pat. No. 5,616,494. Other examples include a thermostable DNA polymerase having sufficient deletions (e.g., N-terminal deletions), mutations, or modifications so as to eliminate or inactivate the domain responsible for the 5'-3' nuclease activity. See, e.g., U.S. Pat. No. 5,795,762.

In some embodiments, the polymerase lacks detectable 3'-5' exonuclease activity. Examples of DNA polymerases substantially lacking the 3'-5' exonuclease activity include the Taq polymerase and its derivatives and any B-family (Type B) polymerase with naturally occurring or engineered deletion of the proofreading domain.

In some embodiments, the polymerase has been modified or engineered to enable or enhance incorporation of nucleotide analogs such as 3'-modified nucleotides; see, e.g., U.S. Pat. Nos. 10,150,454, 9,677,057, and 9,273,352.

In some embodiments, the polymerase has been modified or engineered to enable or enhance incorporation of nucleotide analogs such as 5'-phosphate-modified nucleotides; see, e.g., U.S. Pat. Nos. 10,167,455 and 8,999,676. In some embodiments, such polymerases are phi29 derived polymerases; see, e.g., U.S. Pat. Nos. 8,257,954 and 8,420,366. In some embodiments, such polymerases are phiCPV4 derived polymerases; see, e.g., U.S. Patent Publication No. US20180245147.

In some embodiments, the polymerase is modified or engineered by selection to successfully incorporate a desired modified nucleotide or to incorporate nucleotides and nucleotide analogs with desired accuracy and processivity. Methods of selecting such modified polymerases are known in the art; see, e.g., U.S. Patent Publication No US20180312904A1, entitled "Polymerase Compositions and Methods of Making and Using Same."

It is to be understood that steps 208 and 210 may be combined or their order reversed.

Optionally, at 212, the fluid chamber 115 may be washed before adding the magnetically-labeled nucleotide precursor at step 214.

At 228, a magnetically-labeled nucleotide precursor is selected for the sequencing cycle. In some embodiments, the magnetically-labeled nucleotide precursor is selected from adenine, guanine, cytosine, thymine, or their equivalents. In some embodiments, the magnetically-labeled nucleotide precursor comprises one of magnetically-labeled dATP, dGTP, dCTP, dTTP, or equivalents. The magnetically-labeled nucleotide precursor may be labeled conventional, natural, unconventional, or an analog nucleotide. The term "conventional" or "natural" when referring nucleotide precursors refers to those occurring naturally (i.e., for DNA these are dATP, dGTP, dCTP and dTTP). The term "unconventional" or "analog" when referring to nucleotide precursors includes modifications or analogues of conventional bases, sugar moieties, or inter-nucleotide linkages in nucleotide precursors. For example, dITP, 7-deaza-dGTP, 7-deaza-dATP, alkyl-pyrimidine nucleotides (including propynyl dUTP) are examples of nucleotides with unconventional bases. Some unconventional sugar modifications include modifications at the 2'-position. For example, ribonucleotides with 2'-OH (i.e., ATP, GTP, CTP, UTP) are unconventional nucleotides for a DNA polymerase. Other sugar analogs and modifications include D-ribosyl, 2' or 3' D-deoxyribosyl, 2',3'-D-dideoxyribosyl, 2',3'-D-didehydrodideoxyribosyl, 2' or 3' alkoxyribosyl, 2' or 3' aminoribosyl, 2' or 3' mercaptoribosyl, 2' or 3' alkothioribosyl, acyclic, carbocyclic or other modified sugar moieties. Additional examples include 2'-$PO_4$ analogs, which are terminator nucleotides. (See, e.g., U.S. Pat. No. 7,947,817 or other examples described herein). Unconventional linkage nucleotides include phosphorothioate dNTPs ([α-S]dNTPs), 5'[α-borano]-dNTPs and [α]-methyl-phosphonate dNTPs.

At 214, the selected magnetically-labeled nucleotide precursor is added to the fluid chamber 115. Solely for purposes of illustration, FIG. 11B assumes that the selected magnetically-labeled nucleotide precursor is adenine ("A").

At 216, sequencing is performed to determine whether the selected magnetically-labeled nucleotide precursor has bound to the polymerase or has been incorporated into the extendable primer. The sequencing step 216 can include multiple sub-steps, as shown in FIG. 10. For example, in the method 200 illustrated in FIGS. 10 and 11A, 11B, 11C, 11D, 11E, and 11F, at sub-step 218 the one or more addressing lines 120 of the apparatus 100 are used to detect a characteristic of the magnetic sensors 105 of the magnetic sensor array 110. As explained above, the characteristic may be, for example, a resistance, a change in resistance, a magnetic field, a change in a magnetic field, a frequency, a change in a frequency, or a noise.

At decision point 220, it is determined whether the detection result indicates that the magnetically-labeled nucleotide precursor has bound to the polymerase or has been incorporated into the extendable primer. For example, the determination may be based on the presence or absence of the characteristic, i.e., if the characteristic is detected, the magnetically-labeled nucleotide precursor is deemed to have bound to the polymerase or to have been incorporated into the extendable primer, and if the characteristic is not detected, the magnetically-labeled nucleotide precursor is deemed not to have bound to the polymerase or have been incorporated into the extendable primer. As another example, the determination may be based on a magnitude or value of the characteristic, e.g., if the magnitude or value is within a specified range, the magnetically-labeled nucleotide precursor is deemed to have bound to the polymerase or have been incorporated into the extendable primer, and if the magnitude or value is not within the specified range, the magnetically-labeled nucleotide precursor is deemed not to have bound to the polymerase or have been incorporated into the extendable primer.

The detection (sub-step 218) and determination (decision point 220) may use or rely on all or fewer than all of the magnetic sensors 105 in the magnetic sensor array 110. The determination of whether the characteristic is present or absent, or the value of the characteristic (decision point 220), may be based on aggregating, averaging, or otherwise processing the detection results (sub-step 218) from some or all of the magnetic sensors 105 in the magnetic sensor array 110.

If, at decision point 220, it is determined that the magnetically-labeled nucleotide precursor has bound to the polymerase or has been incorporated into the extendable primer (e.g., the upper path shown in FIGS. 11B, 11C, and 11D), then at step 222, an indication of a complementary base of the magnetically-labeled nucleotide precursor is recorded in a record of the nucleic acid sequence of the nucleic acid strand.

In some embodiments, the magnetically-labeled nucleotide precursor is nonextendable by the nucleic acid polymerase, and, therefore, after detecting the characteristic, the magnetic label must be removed to render the magnetically-labeled nucleotide precursor extendable by the nucleic acid polymerase. In some embodiments, a moiety of the first magnetically-labeled nucleotide precursor is not extendable by the nucleic acid polymerase, and the moiety of the first magnetically-labeled nucleotide precursor is rendered extendable by chemical cleavage. As illustrated in FIG. 10, if additional sequencing cycles are to be performed (i.e., the "No" path of the decision point 224), the magnetic label is removed at 226 using any suitable means (e.g., chemically, enzymatically, or by other means). FIG. 11F provides a graphical illustration of the removal of the magnetic label.

After the magnetic label has been removed at 226, another magnetically-labeled nucleotide precursor is selected at 228. The newly-selected magnetically-labeled nucleotide precursor, which may be the same as or different from the one used in the just-completed cycle, is then added to the fluid chamber 115 at step 214, and the sequencing step 216 is performed again to determine whether the newly-selected magnetically-labeled nucleotide precursor has bound to the polymerase or has been incorporated into the extendible primer.

Figure 11A:
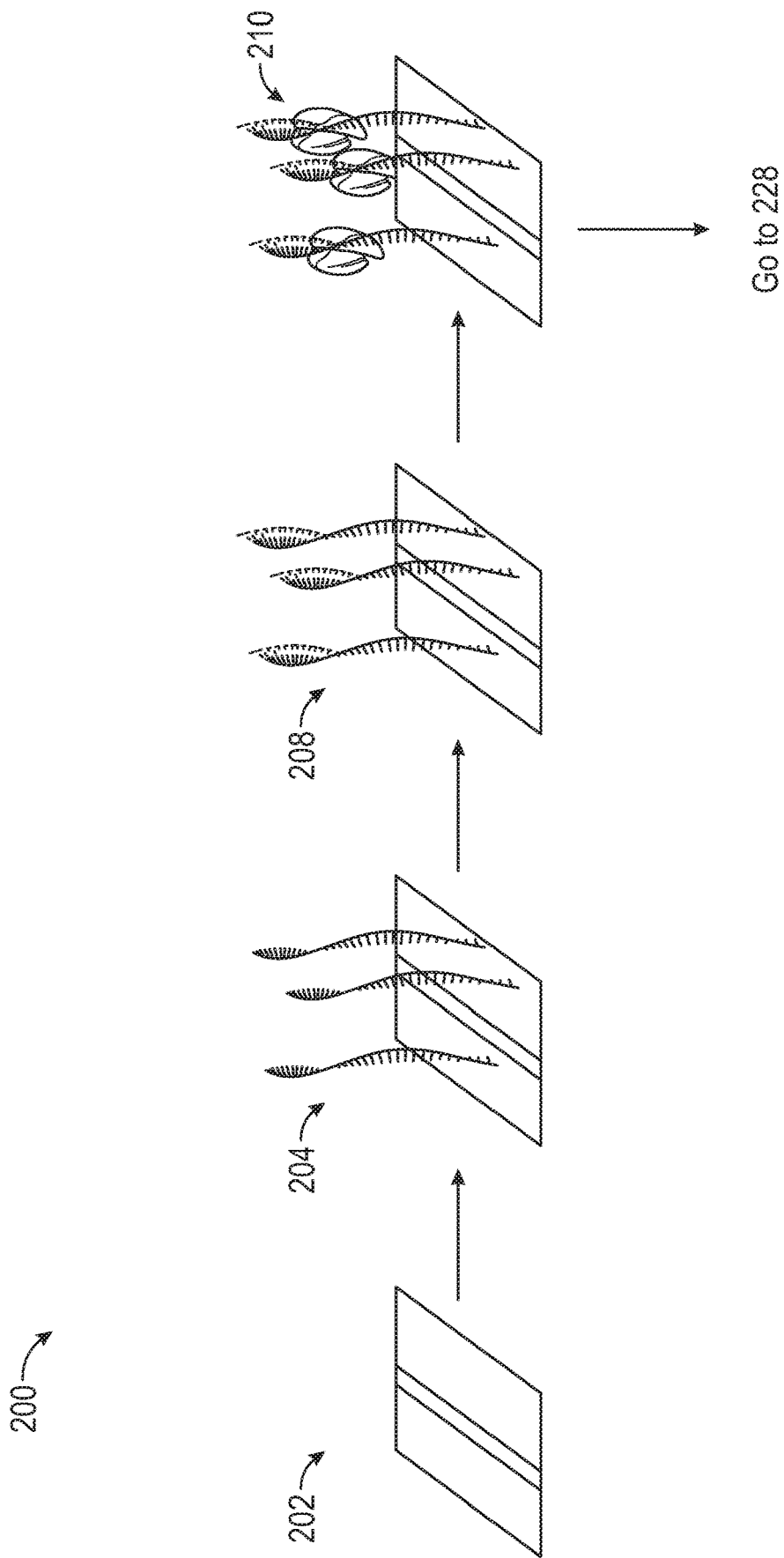
Figure 11B:
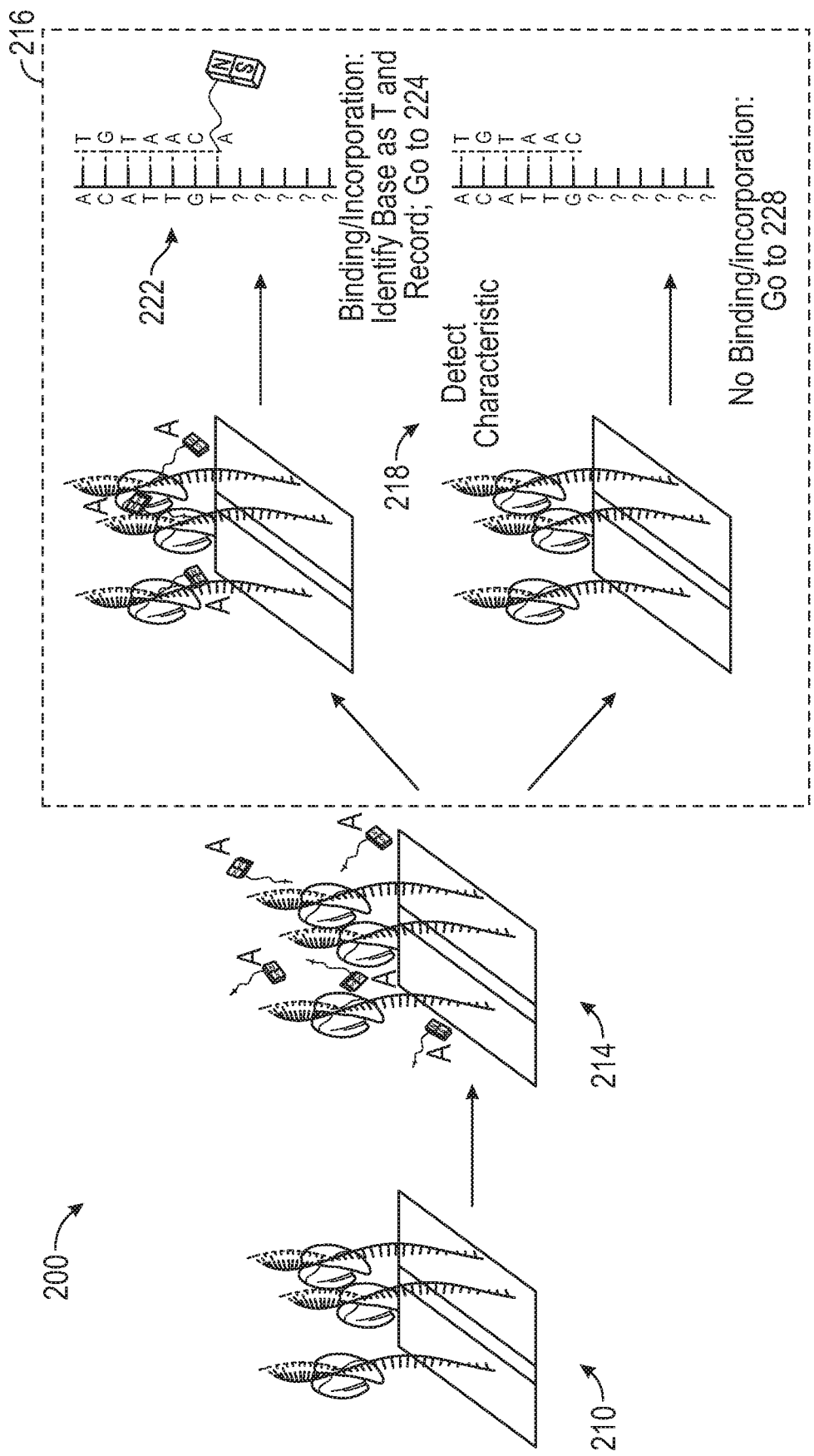
Figure 11D:
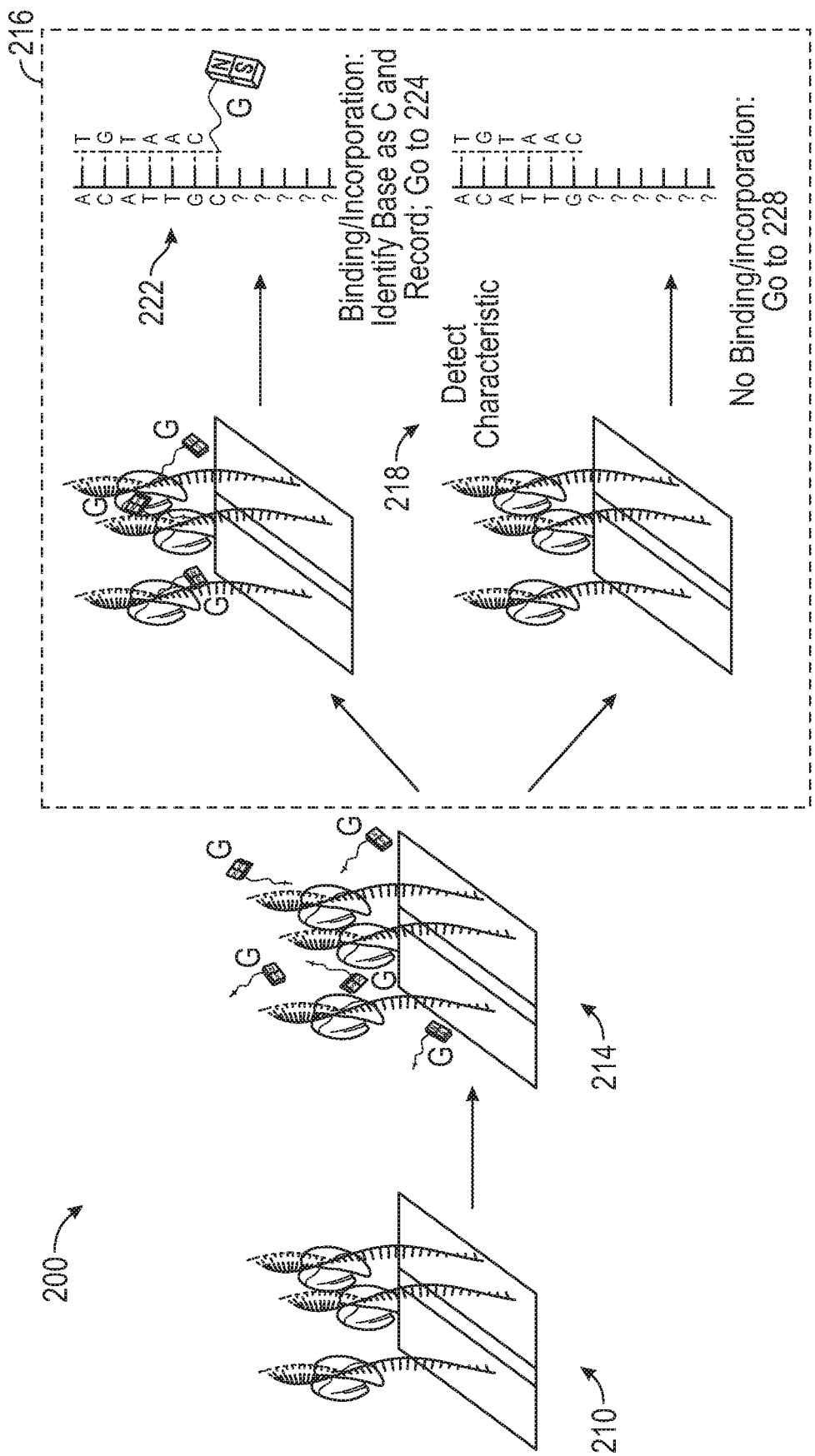

If, at decision point 220, it is determined that the magnetically-labeled nucleotide precursor has not bound to the polymerase and has not been incorporated into the extendable primer (e.g., the lower path shown in FIGS. 11B, 11C, and 11D), the method moves to step 228, where another magnetically-labeled nucleotide precursor is selected. In this case, because the previously-tried magnetically-labeled nucleotide precursor was not a match, the selected magnetically-labeled nucleotide precursor should be different from the one used in the just-completed cycle. For example, FIG. 11C, which follows the lower path of FIG. 11B, assumes that the next magnetically-labeled nucleotide precursor is cytosine. FIG. 11D, which follows the lower path of FIG. 11C (i.e., the previously-selected magnetically-labeled nucleotide precursor (adenine) did not bind to the polymerase and was not incorporated into the extendable primer), assumes that the next magnetically-labeled nucleotide precursor is guanine. Finally, FIG. 11E, which follows the lower path of FIG. 11D (i.e., the previously-selected magnetically-labeled nucleotide precursor (guanine) did not bind to the polymerase and was not incorporated into the extendable primer), assumes that the next magnetically-labeled nucleotide precursor is thymine. It is to be understood that FIGS. 11A, 11B, 11C, 11D, 11E, and 11F illustrate one example of how the apparatus 100 may be used to perform nucleic acid sequencing and are not intended to be limiting (e.g., the order in which the different magnetically-labeled nucleotide precursors are added is arbitrary).

Although FIG. 10 shows a single optional wash step 212 occurring between steps 210 and 214, it is to be understood that additional wash steps may be included in the method. For example, the fluid chamber 115 may be washed between steps 228 and 214 or after step 226 (i.e., to substantially remove the previously-introduced magnetically-labeled nucleotide precursor and any magnetic labels removed in step 226).

At 230, the method 200 ends.

It is to be understood that after some number of sequencing cycles, it may be desirable or necessary to perform step 210 to add additional molecules of the nucleic acid polymerase to the fluid chamber 115 to replenish the polymerase.

FIG. 10, discussed above, illustrates a static SBS embodiment in which magnetically-labeled nucleotide precursors are introduced one at a time. In other static SBS embodiments, multiple nucleotide precursors (e.g., two, three, or four nucleotide precursors) are introduced at once. In such embodiments, different magnetic labels are used for different nucleotide precursors that are introduced at the same time. Each of the introduced precursor's magnetic label has a different magnetic property that enables the magnetic sensors 105 to distinguish between the different magnetic labels used for the different nucleotide precursors that are introduced at the same time.

Figure 12:
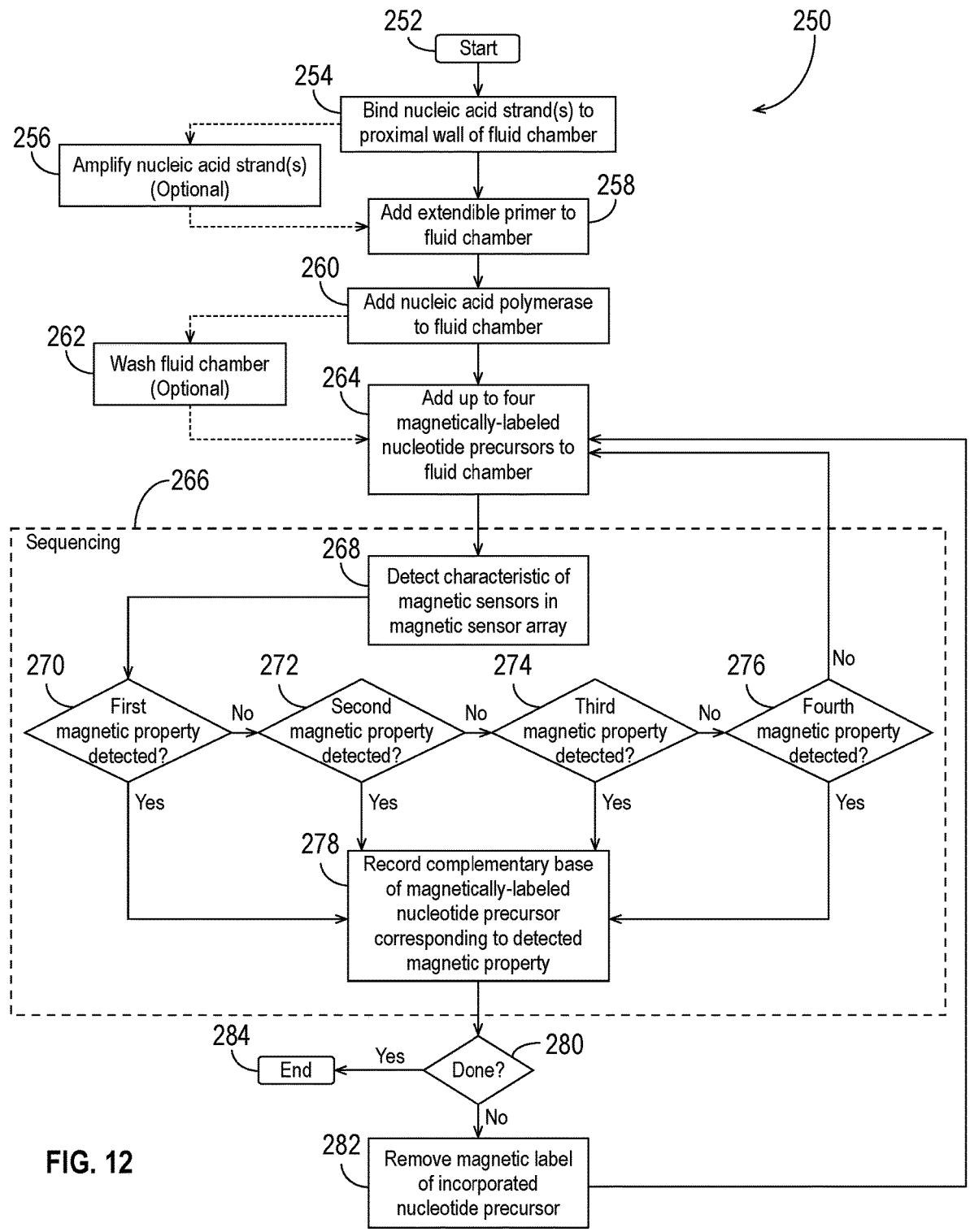
FIG. 12 illustrates an embodiment of a static SBS method in accordance with some embodiments.

FIG. 12 illustrates an embodiment of a static SBS method 250 in which multiple nucleotide precursors are introduced simultaneously. For illustration purposes FIG. 12 shows four nucleotide precursors introduced at the same time, but it is to be understood that the disclosed method can be used to test for more or fewer than four nucleotide precursors.

At 252, the method 250 begins. Steps 254, 256, 258, 260, and 262 are the same as steps 204, 206, 208, 210, and 212 shown and described in the context of FIG. 10. That description is not repeated here.

At step 264, up to four magnetically-labeled nucleotide precursors are added to the fluid chamber 115 of the apparatus 100. Each of the added magnetically-labeled nucleotide precursors is labeled with a different magnetic label so that the magnetic sensors 105 can distinguish between the different magnetically-labeled nucleotide precursors. Specifically, each of the magnetic labels has a different and distinguishable magnetic property (e.g., a first magnetic label used for the first magnetically-labeled nucleotide precursor has a first magnetic property, the second magnetic label used for the second magnetically-labeled nucleotide precursor has a second magnetic property, etc.).

At 266, sequencing is performed to determine which of the added magnetically-labeled nucleotide precursors has bound to the polymerase or incorporated into the extendable primer. The sequencing step 266 can include multiple sub-steps, as shown in FIG. 12. For example, in the method 250 illustrated in FIG. 12, at sub-step 268 the one or more addressing lines 120 of the apparatus 100 are used to detect a characteristic of the magnetic sensors 105 of the magnetic sensor array 110, where the characteristic identifies the magnetic property of the incorporated magnetically-labeled nucleotide precursor. As explained above, the characteristic may be, for example, a resistance, a change in resistance, a magnetic field, a change in a magnetic field, a frequency, a change in a frequency, or a noise.

At decision point 270, it is determined whether a first magnetic property has been detected, where the first magnetic property indicates that the first magnetically-labeled nucleotide precursor has bound to the polymerase or has been incorporated into the extendable primer. The determination may be based, for example, on the presence or absence of the first magnetic property, i.e., if the first magnetic property is detected, the first magnetically-labeled nucleotide precursor is deemed to have bound to the polymerase or have incorporated into the extendable primer, and if the first magnetic property is not detected, the first magnetically-labeled nucleotide precursor is deemed not to have bound to the polymerase or incorporated into the extendable primer. As another example, the determination may be based on a magnitude or value of the first magnetic property, e.g., if the magnitude or value is within a specified range, the first magnetically-labeled nucleotide precursor is deemed to have bound to the polymerase or incorporated into the extendable primer, and if the magnitude or value is not within the specified range, the first magnetically-labeled nucleotide precursor is deemed not to have bound to the polymerase or incorporated into the extendable primer.

If it is determined at decision point 270 that the first magnetic property has been detected, the method moves to step 278, where a complementary base of the first magnetically-labeled nucleotide precursor is recorded in a record of the nucleic acid sequence of the nucleic acid strand.

If, at decision point 270, it is determined that the first magnetic property has not been detected, the method 250 moves to decision point 272, at which it is determined whether a second magnetic property has been detected, where the second magnetic property indicates that the second magnetically-labeled nucleotide precursor has bound to the polymerase or incorporated into the extendable primer. The determination may be made in any the ways described above for the determination of the first magnetic property. If it is determined at decision point 272 that the second magnetic property has been detected, the method moves to step 278, where a complementary base of the second magnetically-labeled nucleotide precursor is recorded in a record of the nucleic acid sequence of the nucleic acid strand.

If, at decision point 272, it is determined that the second magnetic property has not been detected, the method 250 moves to decision point 274, at which it is determined whether a third magnetic property has been detected, where the third magnetic property indicates that the third magnetically-labeled nucleotide precursor has bound to the polymerase or incorporated into the extendable primer. The determination may be made in any the ways described above for the determination of the first magnetic property. If it is determined at decision point 274 that the third magnetic property has been detected, the method moves to step 278, where a complementary base of the third magnetically-labeled nucleotide precursor is recorded in a record of the nucleic acid sequence of the nucleic acid strand.

Finally, if, at decision point 274, it is determined that the third magnetic property has not been detected, the method 250 moves to decision point 276, at which it is determined whether a fourth magnetic property has been detected, the method moves to step 278, where a complementary base of the fourth magnetically-labeled nucleotide precursor is recorded in a record of the nucleic acid sequence of the extendable primer. The determination may be made in any the ways described above for the determination of the first magnetic property. If it is determined at decision point 276 that the fourth magnetic property has been detected, the method moves to step 278, where a complementary based of the third magnetically-labeled nucleotide precursor is recorded in a record of the nucleic acid sequence of the nucleic acid strand. If, at decision point 276, it is determined that the fourth magnetic property has not been detected, the method 250 moves back to step 264.

The detection (sub-step 268) and determinations (decision points 270, 272, 274, and 276) may use or rely on all or fewer than all of the magnetic sensors 105 in the magnetic sensor array 110. The determination of whether a particular magnetic property is present or absent, or the value of the characteristic, may be based on aggregating, averaging, or otherwise processing the detection results (sub-step 268) from some or all of the magnetic sensors 105 in the magnetic sensor array 110.

In the embodiment illustrated in FIG. 12, the determination of which of the added magnetically-labeled nucleotide precursors has bound to the polymerase or has been incorporated into the extendable primer is the result of a separate "yes/no" determination for each of the candidate magnetically-labeled nucleotide precursors. It is to be appreciated that the determination can alternatively be made in a single step, such as, for example, by comparing a value of the detected characteristic to a key. For example, the key can indicate that if the characteristic detected by the magnetic sensors 105 has a value in a first range, a first magnetically-labeled nucleotide precursors has bound to the polymerase or incorporated into the extendable primer; if the characteristic detected by the magnetic sensors 105 has a value in a second range, a second magnetically-labeled nucleotide precursors has bound to the polymerase or incorporated into the extendable primer; if the characteristic detected by the magnetic sensors 105 has a value in a third range, a third magnetically-labeled nucleotide precursors has bound to the polymerase or incorporated into the extendable primer; and if the characteristic detected by the magnetic sensors 105 has a value in a fourth range, a fourth magnetically-labeled nucleotide precursors has bound to the polymerase or incorporated into the extendable primer. The value of the characteristic may be based on aggregating, averaging, or otherwise processing the detection results (sub-step 268) from some or all of the magnetic sensors 105 in the magnetic sensor array 110.

As explained above, in some embodiments, the magnetically-labeled nucleotide precursor is nonextendable by the nucleic acid polymerase, and, therefore, after detecting the characteristic, the magnetic label must be removed to render the magnetically-labeled nucleotide precursor extendable by the nucleic acid polymerase. In some embodiments, a moiety of the first magnetically-labeled nucleotide precursor is not extendable by the nucleic acid polymerase, and the moiety of the first magnetically-labeled nucleotide precursor is rendered extendable by chemical cleavage. In embodiments in which the magnetically-labeled nucleotide precursor is nonextendable by the nucleic acid polymerase, after the record of the nucleic acid sequence of the nucleic acid strand has, at step 278, been augmented (or begun), at decision point 280 it is determined whether additional sequencing cycles are to be performed. If so (the "No" branch of decision point 280), the magnetic label of the incorporated nucleotide precursor is removed. The magnetic label may be removed chemically, enzymatically, or by other means known in the art, and the method 250 proceeds to step 264, where up to four magnetically-labeled nucleotide precursors are added to the fluid chamber 115 (potentially after performing a washing step similar or identical to the illustrated step 262). The sequencing step 266 is then performed again to identify the next magnetically-labeled nucleotide precursor to bind to the polymerase.

If, at decision point 280, it is determined that no additional sequencing cycles are to be performed (the "Yes" branch of decision point 280), the method 250 ends at 284.

As described above, in static SBS, nucleic acid sequencing is performed one magnetically-labeled nucleotide precursor at a time. As a result, the sequencing process is slow but accurate. In contrast, dynamic SBS, as described below, is faster and allows longer base reads, but it is more prone to errors.

Figure 13:
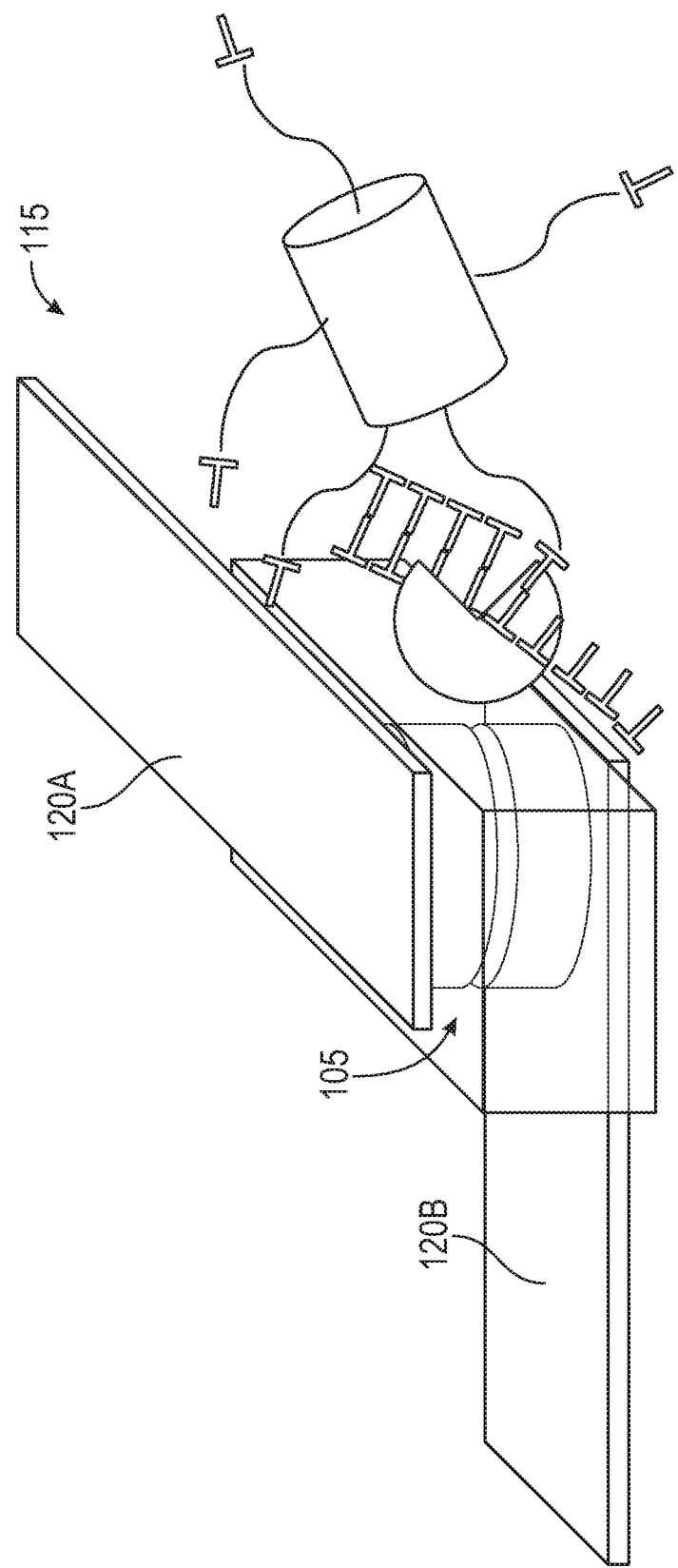
FIG. 13 illustrates dynamic SBS in accordance with some embodiments.

In dynamic SBS, nucleic acid (e.g., DNA) can be sequenced using immobilized polymerase molecules that are tethered to the apparatus 100 in the proximity of the magnetic sensors 105 of the magnetic sensor array 110, as illustrated in FIG. 13. All magnetically-labeled nucleotide precursors may then be added to the fluid chamber 115 at the same time, and detection may be performed in real time at a frequency that is at least as high as the expected rate of incorporation. In some embodiments, detection is performed at least 1,000 times per second (i.e., the detection rate is at least 1 kHz).

In some dynamic SBS embodiments, the nucleotide precursors are distinguished by having different labels, each having a distinct magnetic property to allow them to be distinguished. In other dynamic SBS embodiments, all of the introduced magnetically-labeled nucleotide precursors have the same label but different dynamics of incorporation. For example, different magnetically-labeled nucleotide precursors may be incorporated at different rates, enabling identification of the magnetically-labeled nucleotide precursors based on their rates of incorporation or the amount of time taken to incorporate. As another example, different magnetically-labeled nucleotide precursors may be characterized by different incorporation profiles in the time domain (e.g., an aspect of the incorporation process as a function of time) or in the frequency domain (e.g., an aspect of the incorporation process as a function of frequency). Thus, the "signatures" or profiles of the incorporation processes (e.g., how the magnetically-labeled nucleotide precursors are incorporated, such as how long it takes) may differ for the magnetically-labeled nucleotide precursors, thus enabling them to be distinguished even when the same magnetic label is used for multiple magnetically-labeled nucleotide precursors.

Because detection is performed in real time, no termination chemistry is required for dynamic SBS.

Figure 14:
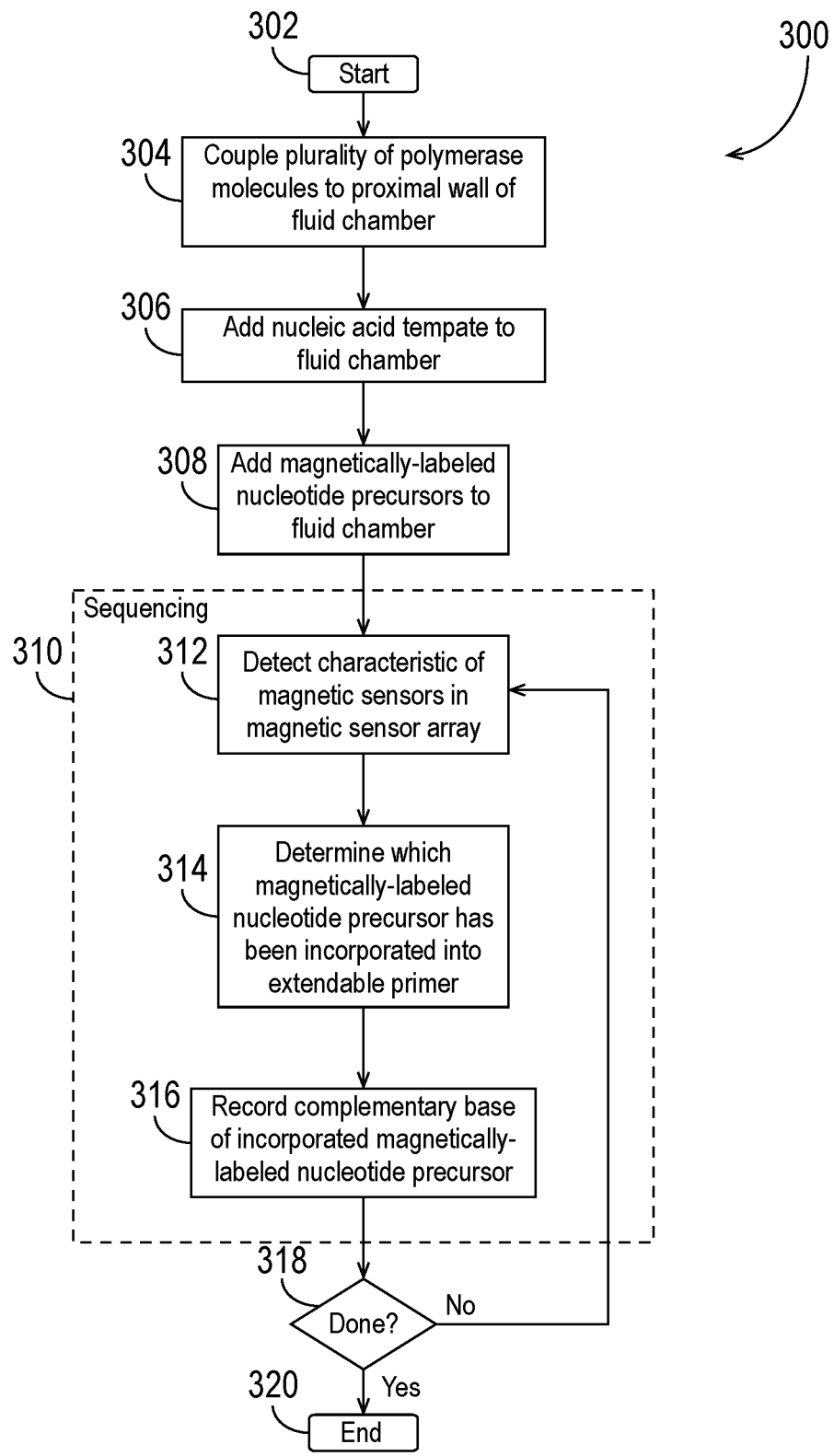
FIG. 14 illustrates a method of dynamic SBS in accordance with some embodiments.
Figure 15:
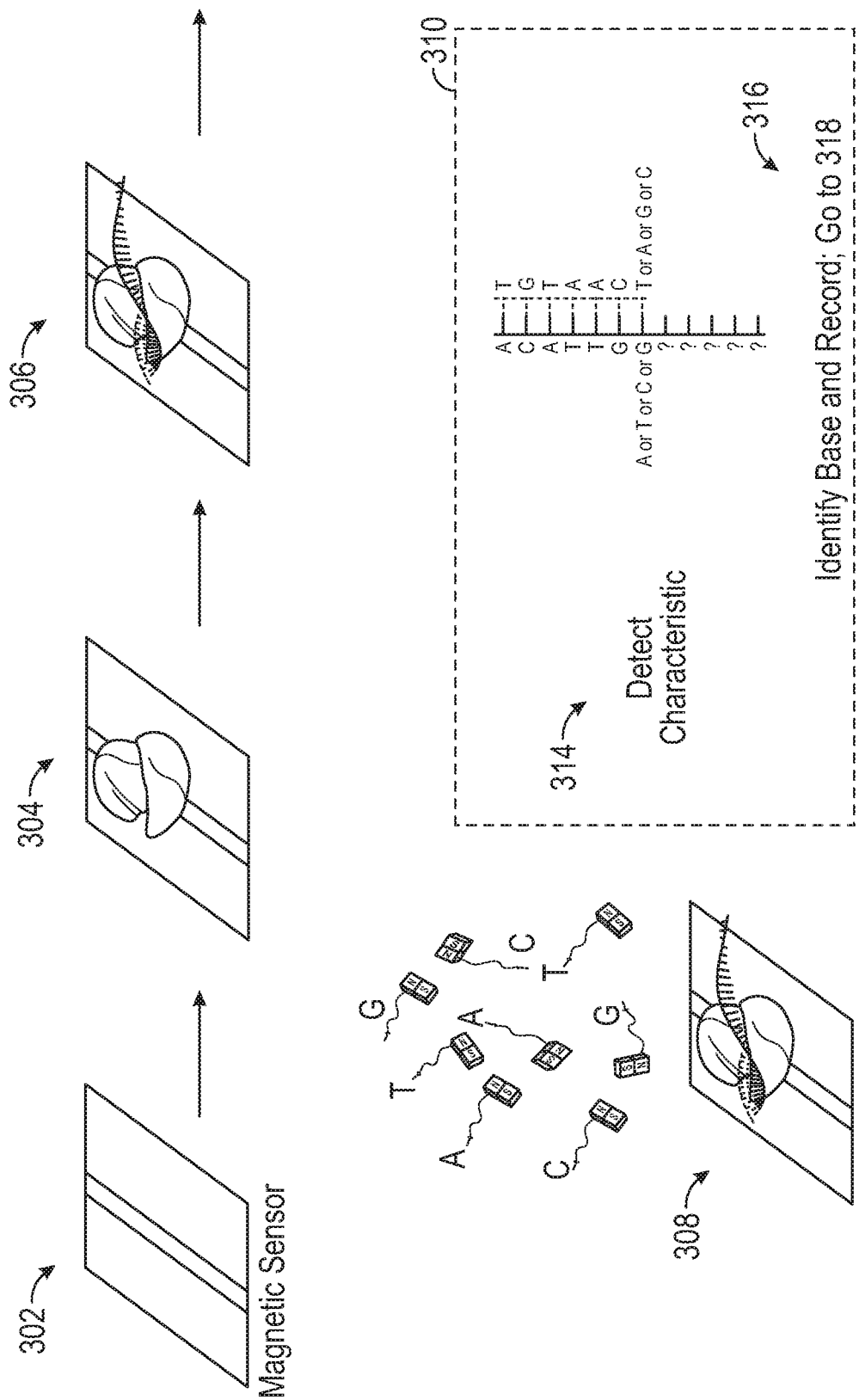
FIG. 15 graphically illustrates the method shown in FIG. 14.

FIG. 14 illustrates a method 300 of dynamic SBS in accordance with some embodiments, and FIG. 15 illustrates the method 300 graphically. At 302, the method begins. At 304, a plurality of polymerase molecules is coupled (tethered) in the proximity of the magnetic sensors 105 of the magnetic sensor array 110. For example, in some embodiments, the polymerase molecules are attached or coupled to the proximal wall 117 of the fluid chamber 115. The polymerase molecules can be attached to the proximal wall 117 using any suitable technique. As one example, the polymerase molecules may be attached by attaching each of the plurality of molecules of the nucleic acid polymerase to a bead, and then attaching the beads to the proximal wall 117 of the fluid chamber 115. The nucleic acid polymerase may be any suitable nucleic acid polymerase, as discussed above in the discussion of FIG. 10. That discussion is applicable here but is not repeated here.

At 306, a nucleic acid template is added to the fluid chamber 115. The nucleic acid template comprises a primer binding site and an extendable primer.

At 308, magnetically-labeled nucleotide precursors are added to the fluid chamber 115. The magnetically-labeled nucleotide precursor may be conventional, natural, unconventional, or an analog, as described above in the context of FIG. 10. In some embodiments, the magnetically-labeled nucleotide precursors are adenine, guanine, cytosine, thymine, or their equivalents. In some embodiments, the magnetically-labeled nucleotide precursors are dATP, dGTP, dCTP, dTTP, or their equivalents. Each magnetically-labeled nucleotide precursor includes a cleavable magnetic label as described above. In the case of four magnetically-labeled nucleotide precursors, a first magnetically-labeled nucleotide precursor comprises a first cleavable magnetic label, a second magnetically-labeled nucleotide comprises a second cleavable magnetic label, a third magnetically-labeled nucleotide comprises a third cleavable magnetic label, and a fourth magnetically-labeled nucleotide comprises a fourth cleavable magnetic label.

It is to be understood that steps 306 and 308 may be combined or their order reversed.

At 310, sequencing is performed to identify which of the first, second, third, or fourth magnetically-labeled nucleotide precursors has been incorporated into the extendable primer. The sequencing step 310 can include multiple sub-steps, as shown in FIG. 14. For example, in the method 300 illustrated in FIG. 14, at sub-step 312 the one or more addressing lines 120 of the apparatus 100 are used to detect a characteristic of the magnetic sensors 105 of the magnetic sensor array 110. As explained above, the characteristic may be, for example, a resistance, a change in resistance, a magnetic field, a change in a magnetic field, a frequency, a change in a frequency, or a noise.

At 314, it is determined which of the first, second, third, or fourth magnetically-labeled nucleotide precursors has been incorporated into the extendable primer during the iteration of the sequencing cycle. For example, the determination may be based on the presence or absence of the characteristic, i.e., if the characteristic is detected, the magnetically-labeled nucleotide precursor is deemed to have been incorporated into the extendable primer, and if the characteristic is not detected, the magnetically-labeled nucleotide precursor is deemed not to have been incorporated into the extendable primer. As another example, the determination may be based on a magnitude or value of the characteristic, e.g., if the magnitude or value is within a specified range, the magnetically-labeled nucleotide precursor is deemed to have been incorporated into the extendable primer, and if the magnitude or value is not within the specified range, the magnetically-labeled nucleotide precursor is deemed not to have been incorporated into the extendable primer. In some embodiments, each of the first, second, third, and fourth cleavable magnetic labels is of a different type, and each type has a different magnetic property that allows the apparatus 100 to distinguish between the first, second, third, and fourth magnetically-labeled nucleotide precursors.

In some embodiments, two or more of the first, second, third, and fourth cleavable magnetic labels have a same specified magnetic property, and sequencing the nucleic acid template is dependent on a dynamic of incorporation (e.g., different magnetically-labeled nucleotide precursors may be incorporated at different rates or take different amounts of time, or be characterized by different incorporation profiles in the time domain or in the frequency domain, etc.). In some such embodiments, each of the first, second, third, and fourth cleavable magnetic labels has a same specified magnetic property, and sequencing the nucleic acid template is dependent on a dynamic of incorporation.

The detection (sub-step 312) and determination (sub-step 314) may use or rely on all or fewer than all of the magnetic sensors 105 in the magnetic sensor array 110. The determination of whether the characteristic is present or absent, or the value of the characteristic (sub-step 314), may be based on aggregating, averaging, or otherwise processing the detection results (sub-step 312) from some or all of the magnetic sensors 105 in the magnetic sensor array 110.

At 316, an indication of a complementary base of the incorporated magnetically-labeled nucleotide precursor is recorded in a record of the nucleic acid sequence.

At 318, if the overall sequencing procedure is not yet complete (the "No" branch of the decision point 318), the method 300 returns to step 312.

When the sequencing procedure is complete or terminated, the method ends at 320.

In the foregoing description and in the accompanying drawings, specific terminology has been set forth to provide a thorough understanding of the disclosed embodiments. In some instances, the terminology or drawings may imply specific details that are not required to practice the invention.

To avoid obscuring the present disclosure unnecessarily, well-known components are shown in block diagram form and/or are not discussed in detail or, in some cases, at all.

Unless otherwise specifically defined herein, all terms are to be given their broadest possible interpretation, including meanings implied from the specification and drawings and meanings understood by those skilled in the art and/or as defined in dictionaries, treatises, etc. As set forth explicitly herein, some terms may not comport with their ordinary or customary meanings.

As used in the specification and the appended claims, the singular forms "a," "an" and "the" do not exclude plural referents unless otherwise specified. The word "or" is to be interpreted as inclusive unless otherwise specified. Thus, the phrase "A or B" is to be interpreted as meaning all of the following: "both A and B," "A but not B," and "B but not A." Any use of "and/or" herein does not mean that the word "or" alone connotes exclusivity.

As used in the specification and the appended claims, phrases of the form "at least one of A, B, and C," "at least one of A, B, or C," "one or more of A, B, or C," and "one or more of A, B, and C" are interchangeable, and each encompasses all of the following meanings: "A only," "B only," "C only," "A and B but not C," "A and C but not B," "B and C but not A," and "all of A, B, and C."

To the extent that the terms "include(s)," "having," "has," "with," and variants thereof are used in the detailed description or the claims, such terms are intended to be inclusive in a manner similar to the term "comprising," i.e., meaning "including but not limited to." The terms "exemplary" and "embodiment" are used to express examples, not preferences or requirements.

The terms "over," "under," "between," and "on" are used herein refer to a relative position of one feature with respect to other features. For example, one feature disposed "over" or "under" another feature may be directly in contact with the other feature or may have intervening material. Moreover, one feature disposed "between" two features may be directly in contact with the two features or may have one or more intervening features or materials. In contrast, a first feature "on" a second feature is in contact with that second feature.

The drawings are not necessarily to scale, and the dimensions, shapes, and sizes of the features may differ substantially from how they are depicted in the drawings.

Although specific embodiments have been disclosed, it will be evident that various modifications and changes may be made thereto without departing from the broader spirit and scope of the disclosure. For example, features or aspects of any of the embodiments may be applied, at least where practicable, in combination with any other of the embodiments or in place of counterpart features or aspects thereof. Accordingly, the specification and drawings are to be regarded in an illustrative rather than a restrictive sense.

The invention claimed is:

1. An apparatus, comprising:
a magnetic sensor array comprising:
a plurality of magnetic sensors, each of the plurality of magnetic sensors coupled to at least one address line, and
at least one selector element;
a fluid chamber adjacent to the magnetic sensor array, the fluid chamber comprising a proximal wall adjacent to the magnetic sensor array; and
sensing circuitry coupled to the magnetic sensor array via the at least one address line, wherein the sensing circuitry is configured to apply a current to the at least one address line to detect a characteristic of at least one of the plurality of magnetic sensors, wherein the characteristic indicates a presence or an absence of a magnetic label in the fluid chamber.

2. The apparatus recited in claim 1, wherein the magnetic sensor array comprises a linear array.

3. The apparatus recited in claim 1, wherein the proximal wall includes a structure configured to anchor nucleic acid or a nucleic acid polymerase to the proximal wall.

4. The apparatus recited in claim 3, wherein the structure comprises a cavity or a ridge.

5. The apparatus recited in claim 1,
wherein the magnetic label is coupled to a nucleotide precursor in the fluid chamber.

6. The apparatus recited in claim 1, wherein the characteristic is a magnetic field or a resistance.

7. The apparatus recited in claim 1, wherein the characteristic is a change in magnetic field or a change in resistance.

8. The apparatus recited in claim 1, wherein each of the plurality of magnetic sensors comprises a magnetic oscillator, and wherein the characteristic is a frequency of a signal associated with or generated by the magnetic oscillator.

9. The apparatus recited in claim 1, wherein the characteristic is a noise level.

10. The apparatus recited in claim 1, wherein a surface of the proximal wall comprises polypropylene, gold, glass, or silicon.

11. The apparatus recited in claim 1, wherein the plurality of magnetic sensors is arranged in a rectangular grid pattern, and wherein the at least one address line includes at least a first address line and a second address line, wherein the first address line identifies a column of the magnetic sensor array and the second address line identifies a row of the magnetic sensor array.

12. A method of manufacturing the apparatus recited in claim 1, the method comprising:
fabricating a first addressing line of the at least one address line on a substrate;
fabricating the plurality of magnetic sensors, each of the plurality of magnetic sensors having a bottom portion and a top portion, wherein each bottom portion is coupled to the first addressing line;

depositing a dielectric material between adjacent magnetic sensors of the plurality of magnetic sensors;

fabricating a plurality of additional addressing lines of the at least one address line, each of the plurality of additional addressing lines coupled to the top portion of a respective magnetic sensor of the plurality of magnetic sensors; and removing a portion of the dielectric material adjacent to the plurality of magnetic sensors to create the fluid chamber.

13. The method recited in claim 12, wherein fabricating comprises depositing.

14. The method recited in claim 12, wherein removing comprises milling or etching.

15. The apparatus recited in claim 3, wherein the fluid chamber further comprises a bottom surface, and wherein the plurality of magnetic sensors is situated behind the proximal wall.

16. The apparatus recited in claim 1, wherein the at least one selector element comprises at least one of a transistor or a diode.

17. The apparatus recited in claim 1, wherein the characteristic is a noise of each of the plurality of magnetic sensors.

18. The apparatus recited in claim 17, wherein the sensing circuitry comprises a heterodyne circuit.

19. The apparatus recited in claim 17, wherein the sensing circuitry comprises:
a comparator, and
a dummy sensor element that does not sense a contents of the fluid chamber.

20. The apparatus recited in claim 1, wherein a first portion of the plurality of magnetic sensors is arranged in a first linear array, and a second portion of the plurality of magnetic sensors is arranged in a second linear array, and wherein the fluid chamber comprises:
a first channel situated between a first side of the first linear array and a first side of the second linear array, and
a second channel situated on a second side of the first linear array or a second side of the second linear array.

21. The apparatus recited in claim 1, wherein the plurality of magnetic sensors is arranged in a cross-point architecture.

22. The apparatus recited in claim 1, wherein each of the plurality of magnetic sensors comprises a spin-torque oscillator (STO), and wherein the characteristic is a change in an oscillation frequency of the at least one of the plurality of magnetic sensors.

23. The apparatus recited in claim 1, wherein a thickness of the proximal wall is between approximately 2 nm and approximately 20 nm.

* * * * *